(12) United States Patent
Davis

(10) Patent No.: US 11,219,627 B2
(45) Date of Patent: Jan. 11, 2022

(54) CLEARANCE OF AMYLOID BETA

(71) Applicant: Synaptec Development LLC, Palm Beach Gardens, FL (US)

(72) Inventor: Bonnie M. Davis, Palm Beach Gardens, FL (US)

(73) Assignee: Synaptec Development LLC, Palm Beach Gardens, FL (US)

( * ) Notice: Subject to any disclaimer, the term of this patent is extended or adjusted under 35 U.S.C. 154(b) by 0 days.

(21) Appl. No.: 14/715,493

(22) Filed: May 18, 2015

(65) Prior Publication Data

US 2015/0328230 A1 Nov. 19, 2015

Related U.S. Application Data

(60) Provisional application No. 61/994,339, filed on May 16, 2014.

(51) Int. Cl.
*A61K 31/55* (2006.01)

(52) U.S. Cl.
CPC .................. *A61K 31/55* (2013.01)

(58) Field of Classification Search
CPC .......... A61K 31/55; A61P 25/00; A61P 25/28
See application file for complete search history.

(56) References Cited

U.S. PATENT DOCUMENTS

| | | | | |
|---|---|---|---|---|
| 5,212,188 A | * | 5/1993 | Caldwell | A61P 25/28 514/343 |
| 6,316,439 B1 | * | 11/2001 | Kosley, Jr. | A61P 25/28 514/215 |
| 6,319,919 B1 | * | 11/2001 | Davis | A61K 31/55 514/215 |
| 8,101,782 B2 | * | 1/2012 | Rupniak | C07C 271/44 540/551 |
| 2012/0244146 A1 | * | 9/2012 | Chain | C07K 16/18 424/133.1 |

FOREIGN PATENT DOCUMENTS

DE WO 2007039138 A1 * 4/2007 ........... A61K 31/343

OTHER PUBLICATIONS

Mattsson et. al., JAMA, 2009, American Medical Association, vol. 302(4), pp. 385-393.*
Seppala et. al., Journal of Alzheimer's Disease, 2011, IOS Press, vol. 25, pp. 583-594.*
Papassotiropoulos et. al., Journal of Clinical Psychiatry, 2006, NIH, vol. 67(4), pp. 652-670 (pp. 1-36 reproduced).*
Schuff et. al., Neurobiology of Aging, 2011, Elsevier, vol. 32, pp. 2318e31-2318e41.*
Takata et. al., 2010, The Journal of Biological Chemistry, American Soc. for Biochemistry and Molecular Biology, vol. 285(51), pp. 40180-40191 (Year: 2010).*
Jack et. al., 2010, Brain: A journal of Neurology, Oxford Univ Press, vol. 133, pp. 3336-3348 (Year: 2010).*
Han et. al., Eur. J. Med. Chem., 1992, Elsevier, vol. 27, pp. 673-687 (Year: 1992).*
Frisoni et. al., Nature Rev. Neurology, 2010, Nature, vol. 6, pp. 67-77 (Year: 2010).*
Bibl et. al., Brain, 2006, Oxford Univ Press, vol. 129, pp. 1177-1187 (Year: 2006).*
Langa et. al., JAMA, 2014, AMA, vol. 312(23), pp. 2551-2561 (Year: 2014).*
Buchhave, P, et al., "Cerebrospinal Fluid Levels of ]-Amyloid 1-42, but Not of Tau, Are Fully Changed Already 5 to 10 Years Before the Onset of Alzheimer Dementia", American Medical Association, 2012, pp. 98-106.
Braak, H., et al., "Neuropathological stageing of Alzheimer-related changes", Acta Neuropathol, 1991, 82, pp. 239-259.
Kerchner, G.A., et al., "Hippocampal CA1 apical neuropil atrophy and memory performance in Alzheimer's disease", Neuroimage, Oct. 15, 2012, 63(1), pp. 194-202.
Grutzendler, J., et al., "Various Dendritic Abnormalities Are Associated with Fibrillar Amyloid Deposits in Alzheimer's Disease", Ann. N.Y. Acad. Sci., 1097, 2007, pp. 30-39.
McDermid, R., "Biospace Market Analysis" Mar. 20, 2015, pp. 1-7.
Marino-Serrais, P., et al., "Layer-Specific Alterations to CA1 Dendritic Spines in a Mouse Model of Alzheimer's Disease", Hippocampus, 2011, 21, pp. 1037-1044.

(Continued)

*Primary Examiner* — Sarah Pihonak
(74) *Attorney, Agent, or Firm* — Ladas & Parry LLP

(57) ABSTRACT

Analogs of (4aS,6R,8aS)-5,6,9,10,11,12-hexahydro-3-methoxy-11-methyl-4aH-[1]benzofuro[3a,3,2-ef][2]benzazepin-6-ol of the formula:

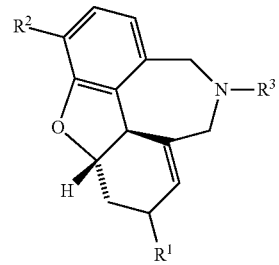

wherein
$R^1$ carbamate, carbonate or carboxlate group;
$R^2$ is alkoxy group of from one to six carbon atoms, a hydroxy group, hydrogen, an alkanoyloxy group or 2 to 10 carbon atoms, a benzoyloxy or substituted benzoyloxy group, a carbonate group of 1 to 10 carbon atoms or a carbamate group such as a mono alkyl or dialkyl or an aryl carbamate wherein the alkyl groups or aryl groups contain from 1 to 10 carbons; and
$R^3$ is hydrogen, alkyl of 1 to 10 carbon atoms, benzyl, cyclopropylmethyl group or a substituted or unsubstituted benzoyloxy group are of use in treating persons meeting criteria for having a risk of developing Alzheimer's type dementia, before symptoms of dementia are observed by reducing the decline of Aβ amyloid CSF.

47 Claims, 11 Drawing Sheets
(8 of 11 Drawing Sheet(s) Filed in Color)

(56) References Cited

OTHER PUBLICATIONS

Hoffmann, V.P., et al., "Effects of Treatment with Solanezumab in Patients with Alzheimer's Disease Who Receive Current Standard of Care", Clinical Trials Conference on Alzheimer's Disease, Nov. 14-16, 2013, 1 page.
Jeffrey, S., "More Positive Data on Aducanumab in Alzheimer's", May 11, 2015, pp. 1-4.
Rees, T., et al., "Acetylcholinesterase promotes beta-amyloid plaques in cerebral cortex", Neurobiology of Aging 24, 2003, pp. 777-787.
Andreasen, N., et al., "Cerebrospinal fluid levels of total-tau, phospho-tau and Ab42 predicts development of Alzheimer's disease in patients with mild cognitive impairment", Acta Neurol Scand 2003, 107 (Suppl. 179), pp. 47-51.
Folstein, M. F., et al., "Mini-Mental State, A Practical Method for Grading the Cognitive State of Patients for the Clinician", J. psychiat. Res., 1975, vol. 12, pp. 189-198.
Buisson, B., et. al., "Open-Channel Blockers at the Human $\alpha4\beta2$ Neuronal Nicotinic Acetylcholine Receptor", Molecular Pharmacology, 53, pp. 555-563 1998.
Haroutunian, V., et al., "Pharmacological Alleviation of cholinergic Lesion Induced Memory Deficits in Rats", Life Sciences, vol. 37, pp. 945-952 1985.
Crum, R.M., et al., "Population-Based Norms for the Mini-Mental State Examination by Age and Educational Level", JAMA, May 12, 1993, vol. 269, No. 18, pp. 2386-2391.
Pavlov, V.A., et al., "Brain acetylcholinesterase activity controls systemic cytokine levels through the cholinergic anti-inflammatory pathway", Brain, Behavior, and Immunity 23 (2009), pp. 41-45.
Arcava, Y., et al., "Memantine Blocks $\alpha7^*$ Nicotinic Acetylcholine Receptors More Potently Than N-Methyl-D-aspartate Receptors in Rat Hippocampal Neurons", The Journal of Pharmacology and Experimental Therapeutics, vol. 312, No. 3, Oct. 28, 2004, pp. 1195-1205.
Ylikoski, R., et al., "Correction for age, education and other demographic variables in the use of the Mini Mental State Examination in Finland", Acta Neurol Scand 1992 85, pp. 391-396.
Aronson, S., et al., "Optimal Dosing of Galantamine in Patients with Mild or Moderate Alzheimer's Disease", Drugs Aging 2009, 26(3), pp. 231-239.
"Additional Results From Phase 3 Trial Of IVIG In Alzheimer's Reported At Alzheimer's Association International Conference", Jul. 16, 2013, pp. 1-4.
"Alzforum Networking for a Cure", Avagacestat, pp. 1-6.
"Pathophilia for the Love of Disease", ICAD 2011, pp. 1-2 2011.
"Bristol-Myers Squibb announces results of BMS-708163 Phase II study on Alzheimer's", Mar. 11, 2013, pp. 1-2 Part 1.
"Bristol-Myers Squibb announces results of BMS-708163 Phase II study on Alzheimer's", Mar. 11, 2013, pp. 1-2 Part 2.
Blennow, K., et al., "Amyloid biomarkers in Alzheimer's disease", Trends in Pharmacological Sciences, May 2015, vol. 36, No. 5, pp. 297-309.
"Intravenous Immune Globulin (IVIG) Study", Alzheimer's Disease Cooperative Study, pp. 1-3.
Friedrich, M. J., "Researchers Test Strategies to Prevent Alzheimer Disease", JAMA, Apr. 23/30, 2014, vol. 311, No. 16, pp. 1596-1598.
Winbland, B., et al. Safety and Efficacy of Galantamine in Subject with Mild Cognitive Impairment, Neurology, 2008; 70/2024-2035.
Scheltens, P. et al. Effect of Galantamine Treatment on Brain Atrophy as Assessed by MRI in Subject with Mild Cognitive Impairment. Presented at the International Conference on Alzheimer's Disease, Philadelphia, Jul. 2004.
Prins, Niels D, et al. The effect of Galantamine on Brain Atrophy Rate in Subjects with Mild Cognitive Impairment is Modified by Apolipoprotein E Genotype: Post-hoc Analysis of Data from a Randomized Controlled Trail 2014.
Janssen-Ortho Inc. Product Monograph Reminyl: galantamine hydrobromide tables 4, mg, 8 mg, 12 mg galantamine base: Reminyl ER: galantamine hydrobromide Extended Release capsules 8 mg, 16 mg, 24 mg galantamine base: cholinesterase Inhibitor. Jul. 2001, revised Jul. 2008.
Goekoop, Rutger, et al. Cholinergic Challenge in Alzheimer Patients and Mild Cognitive Impairment Differentially Affects Hippocampal Activation—A Pharmacological fMRI Study. Brain (2006) 12, 141-147.
David, Kenneth L. et al. Cholinergic Markers in Elderly Patients with Early Signs of Alzheimer Disease. JAMA, Apr. 21, 1999—vol. 281, No. 15: 1401-1406.
Feldman, Howard H. et al. Effect of Rivastigmine on Delay to Diagnosis of Alzheimer's Disease from Mild Cognitive Impairment: The InDDEx Study. Lancet Neurol 2007: 6: 501-12. May 2007.
Supplementary online data. The Lancet Neurology-D-07-00083. 2008.

* cited by examiner

Figure 1

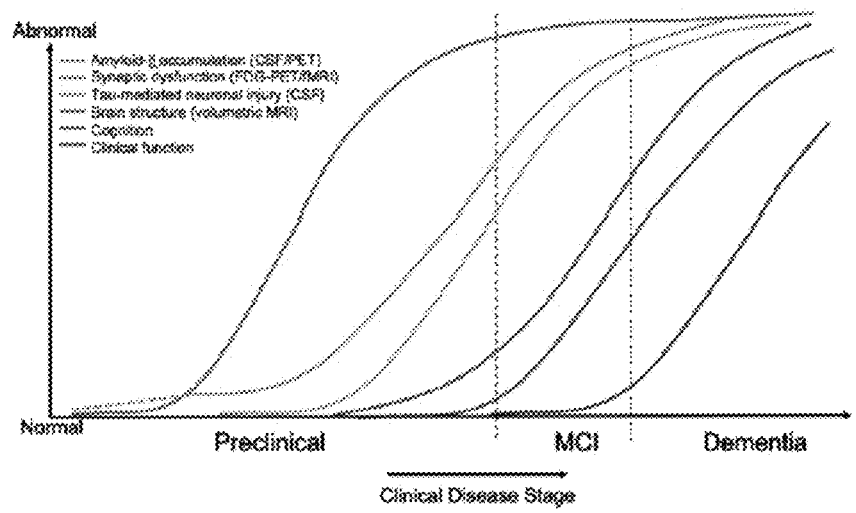

Fig. 3. Hypothetical model of dynamic biomarkers of the AD expanded to explicate the preclinical phase: Aβ as identified by cerebrospinal fluid Aβ$_{42}$ assay or PET amyloid imaging. Synaptic dysfunction evidenced by fluorodeoxyglucose (F18) positron emission tomography (FDG-PET) or functional magnetic resonance imaging (fMRI), with a dashed line to indicate that synaptic dysfunction may be detectable in carriers of the e4 allele of the apolipoprotein E gene before detectable Aβ deposition. Neuronal injury is evidenced by cerebrospinal fluid tau or phospho-tau, brain structure is evidenced by structural magnetic resonance imaging. Biomarkers change from normal to maximally abnormal (y-axis) as a function of disease stage (x-axis). The temporal trajectory of two key indicators used to stage the disease clinically, cognitive and behavioral measures, and clinical function are also illustrated. Figure adapted with permission from Jack et al [22].

Figure 2. Comparison of Clinical, Cognitive, Structural, Metabolic, and Biochemical Changes as a Function of Estimated Years from Expected Symptom Onset.

Fig 4. Compound 5 injected 3.5 h before acquisition improves the 24-h retention of BF-lesioned mice on a passive avoidance task. Mean scores (± SEM) and the number of subjects per dose are indicated. The latencies varied significantly with drug dose ($F = 3.82$, $P = 0.041*$) and the 0.5 mg/kg dose was significantly better than other dose (Scheffe's $F$-test = 3.88, $P < 0.05$).

Photographs of cultured neurons injured by Aβ oligomers, and protected by BDNF and SDL 11349.

Representative laser-scanning confocal micrograph of apical dendrite from a pyramidal neuron in the CA1 region of the dorsal hippocampus showing multiple dendritic spines SDL 11349 treatment for 5 days increases the number of spines on apical dendrites of pyramidal neurons in the CA1 region of the dorsal hippocampus of the mouse SDL11349 treatment for 5 days increases mature spines on apical dendrites of CA1 pyramical neurons in the dorsal hippocampus of the mouse

CLEARANCE OF AMYLOID BETA

RELATED APPLICATION

This application claims priority from U.S. application 61/994,339 filed on May 16, 2014, the contents of which are incorporated herein by reference.

FIELD OF THE INVENTION

In broad concept, the present invention provides a method of treating certain persons who meet criteria for having a risk of developing dementia, and in particular Alzheimer's type dementia, before symptoms of dementia are observed with the objective of delaying the onset of such dementia by administration of certain compounds so as to reduce levels of soluble Aβ oligomers and deposits of Aβ aggregates in the brain and to protect neurite networks and dendritic spines.

BACKGROUND OF THE INVENTION

It has long been known that plaques occur in the brains of persons suffering from Alzheimer's disease (AD). However, the role of such plaques in the etiology of the disease has been unclear.

In the 1980s, the plaques were found to contain beta amyloid (Aβ), whose sequence led to the cloning of the parent molecule, amyloid precursor protein (APP). The soluble form of Aβ is a multifunctional peptide believed to exist in both monomeric and oligomeric forms that perform a number of biological functions. A tiny minority of AD cases could be ascribed to mutations in APP or in the enzymes or enzyme complexes leading to the generation of beta amyloid from APP. Aβ itself could be found in cerebrospinal fluid (CSF) and blood and, surprisingly, was decreased in the CSF of patients with Alzheimer's disease. Large amounts of Aβ, or Aβ oligomers were neurotoxic, while normal amounts were needed for neuronal survival. In 2003, it was first reported that plaques could be visualized in brain in living patients. Later, plaques were seen in asymptomatic people and correlated with anatomical and cognitive decline. Aβ deposits visualized in brain were found to correlate inversely with Aβ concentrations in CSF, such that Aβ deposition in brain, or its decrease in CSF, which are highly correlated and can substitute for each other diagnostically (Weigand et al, Alzheimer's & Dementia 2011, 7, 133) could indicate the beginning of the Alzheimer-type pathological cascade. At that point, it became important to replace the long-established AD diagnostic criteria with classifications that would reflect the extraordinary increase in biological information available, and be useful for research and potential therapeutic purposes.

In 1984, diagnostic criteria for possible, probable and definite Alzheimer's disease, established by a Workgroup of the National Institute of Neurological and Communicative Disorders and the Alzheimer's Disease and Related Disorders Association, were published. These criteria, known as the McKhann criteria, required the presence of dementia in living persons for a diagnosis of probable AD, and biopsy or autopsy tissue confirmation for the diagnosis of definite Alzheimer's disease. (McKhann et al, Neurology 1984, 34, 7, 939) The terms "mild cognitive impairment" and "senile dementia-Alzheimer type" started to come into use, but the view was that an autopsy or biopsy was necessary for a definitive determination of whether a person had suffered from AD. Later, Petersen et al provided a clinical definition for mild cognitive impairment (MCI). (Arch Neurol 1999, 56, 3, 303). The differentiation of those MCI subjects who would and would not convert to AD was markedly improved by the advent of biomarkers, in particular a ligand for amyloid plaques, visible on PET scan, Pittsburgh Compound B (PIB). Biomarkers in cerebrospinal fluid (CSF) were also predictive such as the ratio of CSF β-amyloid protein 1-42 to phosphorylated tau ($A\beta_{1-42}1$ ptau) as to those patients suffering with MCI who would develop AD. (Buchhave, Arch Gen Psychiat 2012, 69, 1, 98).

PIB scans performed in healthy elderly have revealed about a third to be PIB positive. This is not surprising, as autopsies have long been known to show amyloid plaques in nondemented elderly dying of other causes. Recent data indicate that cognitively normal elderly with high PIB uptake have deficits in episodic memory in comparison to those with low uptake, and that difficult face-name retrieval is deficient when brain areas associated with memory systems have Aβ deposits, indicated by PIB retention. (Pike et al, Brain 2007, 130(Pt11) 2837; Rentz et al, Neuropsychologia 2011, 49, 9, 2776) Reduced confidence about memory in elderly normals was associated with greater PIB uptake in prefrontal cortex, anterior and posterior cingulate gyri and the precuneus. (Perrotin et al, Arch Neurol 2012, 69, 2, 223) PIB retention had an anatomic correlate as well, being proportional to cortical thinning in normal subjects. (Becker et al, Ann Neural 2011, 69, 6, 1032) PIB positivity in normals has ominous implications. People with Initial elevations in PIB retention increased their PIB retention at greater rates than those with low binding when re-scanned at 18-20 months and showed accelerated atrophy on MRI. Twenty-five percent of PIB positive healthy controls had MCI or AD by three years, while only 2% of PIB negative people progressed to MCI. (Villemagne et al, Ann Neurol 2011, 69, 181; Sojkova et al, Arch Neural 2011, 68, 5, 644; Chetelat et al, Neurology 2012, 78, 7, 477) Consequently, investigators have stated that "early intervention trials are warranted for individuals with cerebral Aβ deposits", and "therapy aimed to reduce the neurodegenerative process should be commenced in presymptomatic individuals with high PIB." (Pike, op cit; Chetelat, op cit).

Thus, the definitions of probable and definite Alzheimer's disease of 1984 are no longer serviceable. The NINCDS-ADRDA (McKhann) criteria requiring histopathologic confirmation for a diagnosis of definite AD have become identifiable during life as biomarkers in imaging and CSF analysis.

Dubois et al (Lancet Neurol 2010, 9, 1118-27) proposed revision of the definition of Alzheimer's disease to take account of recent advances in biomarkers for the disease and provide a lexicon that encompasses both "predementia and dementia phases".

Sperling et al (Alzheimer's and Dementia 2011, 7, 280), while noting that more work is needed, proposed new definitions that would take into account "biomarkers of AD that take provide in vivo evidence of the disease" and provide criteria which could support studies of "the potential for drugs to intercede in the pathogenic cascade of the disease." The term "Alzheimer's disease" as a clinical disorder would encompass the clinical syndromes that have been NINCDS-ADRDA 'probable Alzheimer's disease' as well as MCI, only insofar as patients have biological evidence in the form of "CSF amyloid 13, total tau, and phospho-tau (ptau); retention of specific PET amyloid tracers, medial temporal lobe atrophy on MRI and/or temporal/parietal hypometabolism on fluorodeoxyglucose PET." Patients corresponding clinically to classical MCI within the diagnosis of "Alzheimer's disease," who do not have loss of instrumental activities of daily living, and do not have a dementia, could be termed "prodromal AD" or "predementia stage of AD".

The term "preclinical Alzheimer's disease" includes two groups. Cognitively normal individuals with amyloid beta evident on PET scans, or changes in CSF Aβ, tau and phospho-tau are defined as being in an "asymptomatic at-risk state for AD". While they are at risk for developing AD, such factors as ApoE status, vascular status, diet, diabetes and others may influence whether they become demented and some will die free of symptoms. The second group is individuals carrying a fully-penetrant dominant autosomal mutation for familial Alzheimer's disease. The term "monogenic AD" is proposed for these people, to differentiate them from people with genetic ApoE types, and they are said to have "presymptomatic AD".

The term MCI would refer to people who don't have an identifiable basis for their symptoms in the form of biomarkers or don't have memory symptoms which are characteristic of AD.

A separate term, Alzheimer's pathology, would refer to plaques, tangles, "synaptic loss and vascular amyloid deposits within the cerebral cortex," whether or not there are clinical manifestations.

In addition to acknowledging the vast increase in knowledge that has occurred since the NINCDS-ADRDA criteria were devised, the new criteria were drafted to facilitate potential course-altering research. Most of the research which has been conducted to date has attempted to decrease Aβ deposits in brain. The very rare monogenic forms of Alzheimer's disease all impact beta amyloid pathways. Down's syndrome, which has a third copy of chromosome 21, on which the gene for amyloid precursor protein (APP) resides, causes an inevitable transition to Alzheimer's disease, with a dementia superimposed on the characteristic intellectual disability, confirmed by plaques and tangles at autopsy. Mutations in the APP molecule are also sufficient to cause Alzheimer's disease. The Swedish mutation increases cleavage by β-secretase, one of the two enzymatic cuts necessary to produce species, and thus increases Aβ production. A newly-described Icelandic mutation impairs the cleavage of APP at the β-secretase site, providing lifelong low levels of Aβ and protection against the development of dementia even in ApoE4+ individuals (Jonsson et al, Nature 2012, 488, 96). The Arctic mutation reduces cleavage by α-secretase, the enzyme which prevents Aβ formation by cutting APP in the middle of the Aβ sequence. The third enzyme involved in the generation or lack of generation of Aβ species is γ-secretase, which produces fragments of various lengths at the carboxy-terminal end. Presenilins (PS) 1 and 2 form part of the γ-secretase complex. Mutations in PS1 or PS2 may increase the amount of or its propensity to oligomerize to form toxic Aβ oligomers, and are fully-penetrant causes of Alzheimer's disease. (reviewed by Benilova et al, Nature Neuroscience 2012, 15, 3, 349, and Cavallucci et al, Mol Neurobiol 2012, 45, 366) Thus, genetically-based increases in the amount or changes in the characteristics of the Aβ species are sufficient to cause classical Alzheimer's disease, and have provided a rationale for numerous clinical trials directed at Aβ.

The vast majority of Alzheimer patients with late-onset AD do not have dominant mutations affecting Aβ. They produce $A\beta_{1-40}$ and $A\beta_{1-42}$ at the same rate as controls. They do, however, have a 30% lower clearance rate of these peptides. (Mawuenyega et al, Science 2010, 330, 1774) A major risk factor for late-onset, or sporadic AD, is the variant of apolipoprotein E (ApoE) which is present. Single nucleotide polymorphisms create ApoE4, ApoE3 and ApoE2 alleles. One copy of ApoE4 increases the risk of developing AD approximately threefold, and two copies increase the risk about 12-fold, (Holtzman et al, Cold Spring Harb Perspect Med 2012; 2:a006312) ApoE2, conversely, reduces the odds ratio to 0.63 as compared to ApoE3. ApoE binds to Aβ peptides and is believed to promote aggregation. E4 positive individuals develop greater amounts of plaque and reduced CSF Aβ whether demented or still cognitively normal. In amyloid-producing transgenic mice, amyloid deposition is greater in those with a human ApoE4 gene than those with ApoE3, and least in those with ApoE2. (Holtzrnan 2012, op cit) These data suggest that ApoE promotes polymerization of Aβ monomers. In addition to promoting aggregation, ApoE appears to influence Aβ clearance. Clearance is decreased in transgenic mice who have human APP and human ApoE4 in comparison to those with ApoE3 or E2, (Castellano et al, 2011, Sci Transi Med 3, 89ra57) Conversely, Aβ clearance has been dramatically enhanced in transgenic mice by a treatment which induces increases in mouse ApoE. (Cramer et al 2012, Science 335, 1503) Thus, multiple lines of evidence implicate Aβ in the pathogenesis of monogenic and sporadic late-onset Alzheimer's disease.

Because of the evidence that increased production, or aggregation of Aβ, or decreased clearance, have been associated with Alzheimer's disease, a variety of approaches to decreasing Aβ has been taken. These are reviewed by Tayeb et al (Pharmacol and Therapeutics 201, 134, 8) and will be summarized here. The first attempt to remove amyloid was by active immunization with AN1792. The study was halted for the occurrence of meningoencephalitis. Antibody responders had a decrease in CSF tau in comparison to placebo patients, but no change in CSF Aβ or ptau. Brain volume loss and ventricular enlargement were increased, while a composite of cognitive tests showed some improvement. (Fox et al, Neurology 2005, 64, 1563) Years later, when a number of these patients had come to autopsy, some of them had extensive clearance of plaques, with no effect on the trajectory of their decline. (Maarouf et al, Molecular Neurodegen 2010, 5, 39) CAD 106 was developed using $A\beta_{1-6}$ as the antigen to avoid the cellular immune response believed responsible for AN1792's meningoencephalitis. CAD 106 was safe and generated an antibody response, but no further results are known. (Winblad et al, Lancet Neurology 2012, 11, 7, 597).

Reduction of the formation of AP has been attempted with compounds that inhibit y-secretase. The first of these, tarenflurbil, an enantiomer of the nonsteroidal anti-inflammatory drug flurbiprofen, was selective in avoiding interference with an important y-secretase substrate, NOTCH, critical to a wide variety of cellular differentiation processes. (Tayeb et al, op cit) Despite encouraging Phase II results, tarenflurbil failed in Phase III. A subsequent study with a nonselective y-secretase inhibitor, semagacestat, which potently decreased CSF Aβ, demonstrated the potential of y-secretase inhibition to cause adverse effects. Two large Phase III trials were terminated because of poorer performance in treated than placebo patients, and an increased incidence of skin cancer. (Tayeb et al, op cit) BMS 708163, avagacestat, is a y-secretase inhibitor which is highly selective for APP over Notch and effectively reduces CSF $A\beta_{40}$. In Phase II studies, skin cancer, which is believed to be Notch-related, occurred, along with rash, pruritis and gastrointestinal ulcers. Amyloid related imaging abnormalities (ARIA, formerly called "vasogenicedema"), like those seen in passive immunotherapy studies, occurred as well.

see internet webpage: news-medical.net/news/20110721/ Bristol-Myers-Squibb-announces-results-of-BMS-708163-Ph ase-II-study-on-Alzheimers.aspx). Cognition trended toward a worsening compared with placebo in the higher dose patients. see internetwebpage: alzforum.org/therapeutics/avagacestat). A trial of BMS 708163 in prodromal Alzheimer's disease for patients having reduced CSF $A\beta_{42}$ showed similar side effects, including non-melanoma skin cancers. There was no reduction in conversion to dementia. Avagacestat produced a small lowering of CSF amyloid and slightly more brain atrophy. The drug's development has been terminated.

While the $A\beta_{1-42}$ measured in CSF in clinical assays is the monomer; there is evidence that dimers and soluble oligomers may be the toxic $A\beta$ species. (Walsh et al, Nature 2002, 416, 535) Thus, preventing $A\beta$ aggregation is another therapeutic strategy. Tramiprosate (Alzhemed™), by mimicking molecules which normally promote amyloid fibril formation, reduced plaque and CSF $A\beta$ in transgenic animals, and CSF $A\beta$ in humans. (Aisen et al, Arch Med Sci 2011, 7, 1, 102) A 78-week study showed a trend towards improvement on the ADAS-cog, no effect on the Clinical Dementia Rating-Sum of Boxes (CDR-SB), and reduction of hippocampal volume loss. Another approach to aggregation inhibition is the use of compounds that block the association of metals with $A\beta$, lowering plaque deposition in transgenic animals and decreasing $A\beta$ toxicity in vitro. (Ritchie et al, Arch Neurol 2003, 60, 1685) Clioquinol, an antibiotic with this property, decreased deterioration on the ADAS-cog in a 36-week study in patients with moderate, but not mild Alzheimer's disease, A second generation compound, PBT2, was tested for 12 weeks in 63 patients with mild AD. At the highest dose of PBT2, two tests of executive function, of 8 components of the Neuropsychological Test Battery (NTB, a battery for milder AD patients), improved significantly, although the statistic did not correct for multiple comparisons. (Lannfelt et al, Lancet Neurol 2008, 7, 779) The ADAS-cog and MMSE changed numerically, although not significantly, in a therapeutic direction, CSF $A\beta_{42}$ decreased significantly, although CSF $A\beta$ levels did not correlate with cognitive effects in a post-hoc reanalysis, (Faux et al, J Alz Dis 2010, 20, 509) ELND005, scyllo-inositol, binds to $A\beta_{42}$, forming a non-toxic complex. It blocks the toxic effects of $A\beta$ oligomers in vitro. In a 78-week study of mild to moderate Alzheimer patients, there was no benefit on any cognitive or behavioral test. Significant decreases in CSF $A\beta$ and increases in ventricular volume occurred, (Salloway et al, Neurology 2011, 77, 1253) A prespecified analysis of mild patients who completed the study showed improvement over placebo on the NTB, with numerically better Alzheimer's Disease Cooperative Study-Activities of Daily Living (ADCS-ADL) performance.

Passive immunization has also been used to attempt to clear $A\beta$, as inhibition of $A\beta$ neuropathology in transgenic mice was achieved by administration of anti-$A\beta$ antibodies. Following an initial positive report, 8 patients were given human pooled immunoglobulin every week to two weeks for six months. CSF $A\beta_{42}$ decreased and there was an increase in the MMSE (MiniMental State Exam) score, greatest for the lowest doses. Three months after the treatments, CSF $A\beta_{42}$ returned to baseline. Cognition did not decline during the no-treatment period in the best responders, those on a low dose of IVIg, only in those on higher doses. Re-institution of therapy at low IVIg doses lowered CSF $A\beta_{42}$ again, and maintained cognition for nine months. The $A\beta$ antibody levels achieved in plasma correlated with dose, but neither was related to the outcomes. (Relkin et al, Neurobiol Aging 2009, 30, 1728) A more recent Phase II report showed no effect on plasma $A\beta$, nor on cognition or function. (http://www.alzforum.org/new/detail.asp?id=3400) IVIg was tested in a large phase III protocol by the Alzheimer's Disease Cooperative Study. see Internet webpage.adcs.org/studies/igiv.aspx) Plasma $A\beta_{42}$ was lowered and fibrillar amyloid (as measured by florbetapir) was reduced at the highest dose, but the ADAS-cog and ADCS-ADL did not change significantly. (see Internet webpage alz.org/aaic/releases 2013/tues 830 am.

Two antibodies engineered to bind to different parts of $A\beta_{1-42}$ have completed phase III trials. Solanezumab is directed at the central portion of $A\beta$. In preclinical studies it cleared plaque in transgenic animals, in a single-dose study, solanezumab raised CSF $A\beta_{42}$ up to 35% in a dose-dependent manner and markedly increased plasma $A\beta_{42}$. (Siemers et al, Clin Neuropharm 2010, 33, 67). CSF tau and ptau were not changed. (Lachno et al, J Alz Dis 2011, 26, 531). In a 12-week phase II trial, solanezumab increased CSF $A\beta_{42}$ but did not affect plaque burden or ADAS-cog. (Solanezumab Phase II abstract P4-346 AAIC 2011, Siemers et al). A low incidence of cerebral vasogenicedema (ARIA) has been reported. see Internet webpage bmartinmd.com/2011/07/icad-2011.html),Two large phase III trials of solanezumab in mild to moderate AD showed 42% (p=0.008) and 20% (p=0.012) reduction in loss on the ADAS-cog in mild patients in Expedition I and Expedition II respectively. Functional decline as measured by the ADCS-ADL was not significantly affected in Expedition I and tended to be in Expedition II, a 19% reduction (p=0.076). When the mild subgroups were combined, cognitive loss was slowed by 34% (p=0.001) and activities of daily living loss was decreased 17% (p=0.057). (newsroom_Lilly_com, Oct. 8, 2012), Neither the Neuropsychiatric Inventory (NPI) nor the CDR-SB was affected. There was a trend for removal of amyloid, only in mild patients. Solanezumab raised plasma and CSF $A\beta$, likely due to bound antibody increasing its half-life. Free $A\beta_{40}$ in CSF was decreased and free $A\beta_{42}$ did not change, nor did tau or ptau. see internet webpage alzforum.org/new/detail.asp?id=3313). There was a trend for a decreased amount of CSF $A\beta$, and a hint of more brain shrinkage in the treated group. Solanezumab has been chosen to be administered to amyloid-positive, nondemented patients overage 70 in the A4 study of the ADCS. see Internet webpage alzforum.org/new/detail.asp?id=3379). A third phase III study, limited to mild AD patients who are amyloid positive, has been initiated. (Alzforum.org/therapeutics/solanezumab).

Bapineuzumab, an antibody to the N-terminus of $A\beta$, also showed no clinical effect at 12 weeks, and at 78 weeks, in a study of 234 patients, the ADAS-cog and Disability Assessment for Dementia (DAD) showed no effect according to the prespecified analysis criteria. However a post-hoc completers analysis favored bapineuzumab, as did an analysis in ApoE4 noncarriers. While there were no overall MRI changes, ApoE4 noncarriers had less brain volume shrinkage on drug than placebo, while carriers had more ventricular enlargement on drug than placebo. (Salloway et al, Neurology 2009, 73, 2061) Bapineuzemab reduced CSF tau significantly and tended to reduce ptau at one year, relative to placebo, without changes in CSF $A\beta$. (Blennow et al, Arch Neurol 2012, 69, 8, 1002) Cortical amyloid reduction progressed with time, and was 25% lower at 78 weeks in treated than in untreated patients, with no effect of E4 status or bapineuzumab dose. (Rinne et al, Lancet Neurol 2010, 9, 363) Bapineuzemab patients did not fare well. A retrospective review of MRIs showed a 17% incidence of vasogenic edema which was related to dose and the ApoE4 allele. (Sperling et al, Lancet Neurology 2012, 11, 241) Bapineuzumab phase III studies were divided into ApoE4 carriers, who received 0.5 mg/kg, and noncarriers, who received 0.5, 1.0 or 2.0 mg/kg, but the highest dose was dropped for amyloid-related imaging abnormalities (ARIA). (Salloway et al, CTAD Presentation, Oct. 29, 2012) Moderate patients, regardless of ApoE status, had no cognitive effect, separately or combined. Mild patients (MMSE≥20) who were ApoE4− had significant improvement on the DAD, but there was no cognitive effect regardless of ApoE status, CSF ptau was decreased with little change in tau. CSF Aβ did not change. (Fox et al, CTAD Presentation, Oct. 29, 2012). Both increased brain volume loss and ventricular volume expansion were seen on drug in the combined studies, with left hippocampal loss in ApoE4− patients. ARIA occurred in about 20% of ApoE4+ patients at low dose, and ApoE4− patients at high dose (Sperling et al, CTAD presentation, Oct. 29, 2012). About ⅓ of ApoE4+ homozygotes had ARIA. Cognitive and functional test scores were not affected by ARIA. Deaths in ApoE4 carriers were 2.2% of bapineuzumab patients as compared to 1.1% of placebo patients, and 2.1% vs 1.3% in noncarriers. The difference in E4+ patients was primarily due to cancer, which did not appear to be treatment-emergent. Seizures were increased as well in the drug groups. Bapineuzumab reduced accumulation of amyloid, primarily in mild patients.

Of the immunologic anti-Aβ therapies, only solanezumab has shown cognitive benefit, less in its second study than its first, and a trend for functional benefit, all in mild patients, in whom it tended to clear plaque. Free CSF Aβ was not restored by any agent. All showed some evidence for increased brain shrinkage. Bapineuzumab cleared plaque and caused ARIA at the most effective doses. Benefits seem to be greatest in mild patients.

As can be surmised from the PIB positivity found in healthy elderly discussed above, Aβ deposition begins decades before the onset of clinical Alzheimer's disease (AD). Changes in the brain are occurring decades before the onset of dementia. The pyramidal cells of the CA1 region of the hippocampus begin to be affected in Braak stage II. (Braak H and Braak E, Acta Neuropathologica 1991, 82, 239-259). In early AD, the stratum radiatum is particularly affected and its width correlates with measures of delayed recall. (Kerchner G A et al, Neuroimage 2012, 63(1): 194-202) Dendritic spines have been shown to be reduced in the vicinity of amyloid deposits in the Alzheimer brain, as shown in frontal cortices and hippocampi. (Gruntzendler et al, Ann NY Acad Sci 2007, 1097, 30-39.) Not surprisingly, in mice transgenic for AD genes, dendritic spines in the stratum radiatum have an increased proportion of small heads, consistent with the long term depression which is seen in models of AD. (Merino-Serrais P, et al, Hippocampus 2011, 21, 1037-1044). The current concept of the time course of the Alzheimer process is shown in FIG. 1. (op cit Sperling et al, 2011) The red line on the left is a measure of amyloid-β accumulation as assessed by either the binding of a PET ligand, or a decrease in CSF Aβ, which are strongly inversely related to each other. (Weigand et al, 2011, op cit) It can be seen that there is little change in Aβ deposition once the diagnosis of clinical Alzheimer's disease is reached. The second line, shown in orange represents the time course of abnormalities in imaging such as fluorodeoxyglucose (FDG) uptake, a measure of brain metabolic activity. People who are PS1 mutation carriers, or who are ApoE4 carriers show reduced FDG uptake before they have notable cognitive symptoms. (Bateman et al, NEJM 2012, 367, 795; Jagust et al, 0.1 Neurosci 2012, 32, 50, 18227).

Bateman et al 2012, (op cit) based on data from members of families possessing autosomal dominant genes for the development of Alzheimer's disease concluded that initially there was a decrease in Aβ42 in CSF followed by fibrillar AB deposition, then increased tau in CSF followed by hippocampal atrophy and hypometabolism, cognitive and clinical changes, as shown in FIG. 2. While most of the biological measurements show statistically-significant differences between the groups 10-15 years before the expected time of disease onset, it can be seen that the changes begin numerically from the earliest time point of the study, 25 years before expected disease onset.

Thus, a possible explanation for the lack of success of anti-amyloid therapies in Alzheimer cohorts is that whatever damage Aβ initiates is mostly complete by the time of frank dementia. Thus, it is felt that earlier intervention, which is now possible because patients destined to get Alzheimer's disease can be identified with CSF measurements or PET ligands for fibrillar β-amyloid, may be more effective. Many anti-Aβ therapies are now in studies of prodromal Alzheimer's disease. Reuters, May 15, 2012, reports a trial being carried out in Medellin, Colombia on a kindred group having a PS1 mutation in an attempt to see whether crenezumab can prevent or slow the disease about five years before the expected onset of symptoms. reviewed in JAMA 2014, 311, 16, 1596 by M J Friederich).

Another reason for the lack of success to date of anti-amyloid therapies may be the loss of the biologic effects of physiologic amounts of the Aβ peptides. As can be seen from FIG. 1, changes in Aβ, seen as increases in PIB binding in cortex, or decreases in CSF Aβ$_{1-42}$ concentrations, are largely established by the onset of classical MCI and continue through the dementia stage. Bateman (op. cit) showed, in patients carrying fully-penetrant Alzheimer's-causing mutations, CSF AB begins to decrease as much as 25 years before the expected onset of dementia. Levels of CSF Aβ$_{1-42}$ do not differ significantly between mutation carriers and noncarriers until 10 years before expected dementia onset because carriers start with elevated levels which fall from the very first study point at −25 years, until they are lower than those of noncarriers.

At the onset of dementia, CSF Aβ$_{1-42}$ is about 45% lower in Alzheimer patients than in controls, and there is little change subsequently. (Op cit Bateman 2012) CSF is in equilibrium with the interstitial fluid (ISF) surrounding the neurons in brain. (Zhang et al 1990, J Anat 170, 111-123) In transgenic mice who have plaques due to an APP mutation, CSF Aβ levels correlate with ISF Aβ levels (measured as Aβ$_{1-28}$ or longer). (Cirrito et al 2003, J Neurosci 23(26): 8844-8853) In these APP transgenic mice, ISF Aβ$_{1-42}$ levels fell as the Aβ deposited in brain parenchyma, with a 50% fall occurring even before the extractable Aβ in deposits increased significantly, (Hong et al, J Neurosci 2011, 31(44): 15861-15869) This transgenic mouse data is analogous to the situation in patients with autosomal dominant Alzheimer's genes having declining CSF Aβ1-42 before plaques can be visualized with PET ligands. Taking the transgenic animal and human data together, it can be presumed that Aβ in the ISF as represented through Aβ levels in CSF, is reduced from physiological levels for many years in those destined to develop Alzheimer's disease.

The exception to sub-physiological levels of Aβ in the ISF would be the "halo" surrounding a plaque. While Aβ in fibrils in plaques is irreversibly bound, (locked), the amyloid core is surrounded by monomeric and oligomeric Aβ species which can dissociate or associate (docked). (op cit Cirrito 2003, op cit Hong 2011). Following administration of a γ-secretase inhibitor to halt Aβ production, ISF Aβ falls more slowly in the presence of plaques than in their absence, indicating that the plaques are contributing Aβ to the ISF. (op cit Cirrito 2003, Hong 2011) Conversely, following administration of labelled $A\beta_{1-40}$, recovery of the label from the ISF is only half as much in plaque-rich mice as in plaque-free mice, while the labelled $A\beta_{1-40}$ can be found in the tissue extracts of the plaque-rich mice. Plaques are therefore a reservoir which can remove and release Aβ and maintain an equilibrium with the ISF, keeping ISF Aβ distant from plaques at low levels. Consequently, the Alzheimer brain can be seen as having excess Aβ species in the vicinity of plaques where there are dystrophic neurons, and subnormal concentrations in healthy tissue.

Functional consequences of Aβ deficiency were first suggested in 1990 by Yankner et al (Science 1990; 250:279) A physiologic concentration of $A\beta_{1-40}$ (60 pM) enhanced the survival of undifferentiated hippocampal neurons in culture, while a markedly supraphysiologic concentration (100 nM) caused mature hippocampal neurons to undergo "collapse of [the] dendritic arbor, axonal retraction . . . and vacuolar inclusions in the somato-dendritic region." These degenerative changes are reminiscent of what is seen in the halo surrounding a plaque. Cultured rat cortical neurons deprived of Aβ functions via γ-secretase inhibition β-secretase inhibition show shrinkage, granularization and decreased viability. A comparable decrease in viability follows the application of the N-terminal Aβ antibody 3D6 (note that this is the rat equivalent of bapineuzumab). The neurons can be rescued by 1 nM $A\beta_{1-40}$. (Plant et al, Neurosci 2003; 23(13): 5531) The toxicity of high concentrations of $A\beta_{1-42}$ may be due to oligomer formation, as a specific small peptide which blocks oligomer formation prevented the loss of neurite outgrowth and synapses exposed to an aged, i.e., oligomer-containing $A\beta_{1-42}$ preparation applied to a cortical culture. (Innocent et al, Neuropharmacology 2010; 59:343) Removal of dimers and larger Aβ species has also prevented the loss of LTP caused by the application of medium from APP-producing cells to rat hippocampus in vivo (Walsh et al, op cit) and a similar toxic effect of extracts from human AD brains. (Shankar et al, Nature Medicine 2008; 14:837). It is not certain, however, that oligomers at all concentrations are toxic. In a series of elegant experiments, it was shown that lowering $A\beta_{1-42}$ below physiological concentrations via siRNA to APP or a specific antibody to mouse $A\beta_{1-15}$ impaired LTP in mouse hippocampal slices, and similarly depleting endogenous $A\beta_{1-42}$ impaired spatial and contextual fear memory in mice. Each of these could be rescued by physiological concentrations of $A\beta_{1-42}$, indicating the necessity of this peptide for learning and memory. The ability of an $A\beta_{1-42}$ preparation to rescue LIP, however, was lost when the preparation was enriched in monomers. (Puzzo et al, Ann Neural 2011; 69: 819) It is possible, therefore, that oligomers which may form in certain Aβ preparations, are involved in their physiological effects. To summarize, the requirement for physiologic concentrations of Aβ for neuronal survival and performance has been repeatedly demonstrated using a variety of approaches.

A similar pattern was shown when wild-type mice received infusions of $A\beta_{1-42}$ via cannula into the hippocampus and were tested for the time to find a submerged platform in the Morris water maze. Mice treated with concentrations of Aβ from 2 pM to 2 nM found the platform more quickly than mice treated with concentrations up to 20 μM, (Puzzo et al, Neurobiol Aging 2012, 1484e15).

Enhanced memory in the physiologic range, and impairment at high concentrations, were similarly demonstrated when trained animals were put into the pool with the platform removed. Animals with normal amounts of A3 peptide spend a greater amount of time in the target quadrant, where the platform had been. Thus, $A\beta_{1-42}$ is a normal constituent of the brain interstitial fluid which is necessary for learning and memory but which in excess can impair neuronal function and survival.

As reviewed above, the Alzheimer brain has very high levels of Aβ species in the vicinity of plaques, and subnormal Aβ concentrations in the ISF as evidenced by low Aβ in CSF. It might therefore be predicted that neurons near plaques will be impaired by excess Aβ, and that neurons distant from plaques will not have enough Aβ to perform optimally. In fact, neurons near plaques may indeed manifest toxicity of Aβ species while neurons further from plaques are abnormally quiet. Recordings from neurons in the frontal cortex of wild type mice showed that 88% demonstrated normal frequencies of calcium transients, representing action potentials, while 10.7% were hypoactive, and 1.3% were hyperactive. In contrast, by 6-8 months of age, when Appswe/PS1 mice have deposited plaque, only 50% of cells demonstrated calcium transients in the normal range, while 29% were hypoactive and 21% were hyperactive. (Busche et al, Science 2008, 321, 1686) The development of hyperactive neurons was strictly correlated with plaque deposition and decrement of performance in the water maze (spatial memory) and Y maze (working memory). Notably, hyperactive neurons were found in the direct vicinity of Aβ plaques, while abnormally quiet neurons increased with the distance from a plaque.

It was suggested that soluble Aβ oligomeric species near plaques could account for the hyperactive neurons. I would suggest that insufficient concentrations of Aβ in the ISF surrounding healthy cells distant from plaques may explain their hypoactivity.

The notion that the Alzheimer brain, and the brain which is developing, but has not yet reached the stage of classical Alzheimer's disease with dementia is impaired by both excess Aβ in the region of plaques, and subnormal Aβ concentrations in the ISF bathing healthy tissue away from plaques, has important treatment implications. The clinical outcome measures used to evaluate interventions designed to alter the course of AD depend on the function of intact, healthy synapses. Anti-amyloid agents would not be expected to target plaques and spare healthy tissue, but rather to further decrease ISF Aβ, which is already reduced to about half of normal in patients with AD or classical MCI. Puzzo and Arancio have suggested that the role of picomolar concentrations of Aβ on synaptic plasticity and memory be taken into consideration where Aβ-lowering therapies are concerned. (J Alz Dis 2013; 33, S111-S120) 3D6, the rat-equivalent of bapineuzemab, impaired neuronal viability, as have large doses of γ- and β-secretase inhibitors. These compounds may be altering plaque, as bapineuzumab has been shown to do, but may at the same time, impair performance on outcome measures in studies and in daily life, and compromise healthy neurons, possibly evidenced by the brain shrinkage seen in immunotherapy studies. The combined solanezumab phase III studies have been analyzed for solanezumab's performance in patients with and without cholinesterase inhibitor and memantine treatments (called standard of care—SOC). (Hoffman V P, Case M, Hake A M, Effects of treatment with solanezumab in patients with Alzheimer's disease who receive current standard of care. Poster presented at Clinical Trials in Alzheimer's Disease, San Diego, November 2013) As shown in Table 4 below, patients not receiving cholinesterase inhibitors deteriorated cognitively by 3.6 points more on the ADAS-cog, and those on memantine only, by 4.1 points more, if they received solanezumab treatment than if they received placebo. Note that few patients did not receive ChEIs likely explaining the lack of statistical significance. (Combining the non-cholinesterase inhibitor groups might be expected to produce a significant result, as the excess decline due to solanezumab was similar in magnitude, and the result in the no standard-of-care (SOC) group was nearly significant.) Patients who did receive cholinesterase inhibitors, without memantine benefitted significantly from solanezumab, by 2.1 points The pattern of numerically impaired performance in solanezumab patients unless ChEIs were co-administered persisted in activities of daily living (the ADCS-ADL). These results would be consistent with solanezumab's binding to soluble Aβ and impairing the function of the healthy neurons responsible for cognition and function. ChEIs might improve the function of the normal cells, allowing the antibody to show a net benefit because of its binding of Aβ where it is toxic. These data suggest the possibility that administration of solanezumab in populations of pre-dementia subjects who are not receiving cholinesterase inhibitors could impair their function and perhaps the health of their normal neurons, advancing the onset of dementia.

TABLE 4

Change from Baseline to Week 80
in ADAS-Cog14 Scores - Overall

| Population | Treatment | n | LS Mean Change (SE) | Value [a] | Value [b] |
|---|---|---|---|---|---|
| No SOC | Solanezumab | 68 | 6.5 (1.3) | .055 | .017 |
|  | Placebo | 65 | 2.9 (1.4) |  |  |
| AChEI only | Solanezumab | 451 | 6.8 (0.5) | .004 |  |
|  | Placebo | 444 | 8.9 (0.5) |  |  |
| Memantine only | Solanezumab | 30 | 11.2 (1.9) | .100 |  |
|  | Placebo | 50 | 7.1 (1.6) |  |  |
| AChEI + Memantine | Solanezumab | 215 | 9.8 (0.8) | .072 |  |
|  | Placebo | 204 | 11.7 (0.8) |  |  |

[a] Differences between Solanezumab and Placebo within SOC subgroups
[b] Differences between Solanezumab and Placebo among SOC subgroups
Bold indicates p < .05

A therapeutic which can discriminate between the Aβ which has become toxic due to high concentration and/or excess oligomerization and the Aβ which supports normal neuronal integrity and function is needed in order to alter the Alzheimer process. In fact, preliminary data on the effect of aducanumab (BIIB037), an antibody to aggregated, but not monomeric Aβ, suggest that the Alzheimer process can be altered by such an agent. The patient population, all florbetapir (amyloid) positive, had an average MMSE of 25, 60% with mild AD, 60% ApoE4+. Groups of 36, 28, 30, 27, or 28 initially received 0, 1, 3, 6, or 10 mg once a month for 6 months to a year. Amyloid measurements in the 10 mg group were reduced nearly to the cutoff for amyloid positivity at one year, with lesser decrements at the lower doses. MMSE decline was reduced about 80%, and CDR-sb decline, about 75% in the 10 mg group. However, 41% of the patients at the 10 mg dose developed ARIA, including 55% of the ApoE4+ patients in this group. The lower doses of aducanumab produced smaller, but significant changes in the outcome measures, and less ARIA. This study provides evidence that a strategy to counteract pathological amyloid species while sparing physiological forms can alter the Alzheimer process. Whether this agent can be used in its most effective form is not clear. (Sevigny, J, Randomized, double-blind, phase 1B study of BIIB037, an anti amyloid beta monoclonal antibody, in patients with prodromal or mild Alzheimer's disease. Presented at the 12th International Conference on Alzheimer's and Parkinson's Diseases, Nice, France, Mar. 18-22, 4015) One aspect of the present invention is a combination of the lower, safer doses, of aducanumab with an agent with a different mechanism of action, such as SDL 11349 described below, to increase efficacy without increasing the toxicity of the antibody.

In my U.S. Pat. No. 4,663,318, I described the use of galantamine, a known cholinesterase inhibitor, in the treatment of Alzheimer's disease. In my PCT publication WO 8808708, I described the use of analogs of galantamine and lycoramine for a similar purpose. In my U.S. Pat. No. 6,670,356, I described the effects of analogs of galantamine and lycoramine in modulation of nicotinic receptors and in treating and retarding the progression of Alzheimer's and Parkinson's diseases, neuroprotection against neurodegenerative disorders. At the time of these patents, Alzheimer's disease understood to be a condition that manifested itself by dementia and its underlying causes were only beginning to be understood. The treatments described in my earlier patents addressed factors involved in such dementia, namely reducing the activity of acetylcholinesterase so as to limit the reduction in availability of the neurotransmitter acetylcholine that arises from the action of acetylcholinesterase thereon and indirect stimulation of nicotinic receptors by allosteric modulation thereof to improve their functioning.

Galantamine has the structure:

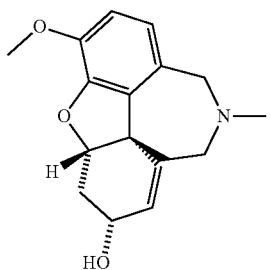

Galantamine is approved for the treatment of patients with mild to moderate Alzheimer's disease. It is administered in a dose of from 16 mg to 24 mg/day. It has been reported that it can reduce deposited Aβ in transgenic mice, and does not change levels of soluble Aβ in these mice. (Takata et al, J Biol Chem 2010, 285, 51, 40180) In addition, it protects neurons against various toxic insults in vitro. Human clinical data in AD patients are consistent with a neuroprotective effect of galantamine in AD patients, however galantamine increased mortality during two separate studies of MCI patients and there is a warning in its labeling regarding its use in MCI.

APdE9 mice, containing Swedish familial APP, and well as presenilin mutations, develop Aβ plaques beginning at 9 months. Mice were treated with saline or galantamine, 1 or 5 mg/kg/day, beginning at 9 months of age for the subsequent 2 months. The 1 mg dose significantly reduced insoluble (fibrillar) Aβ$_{1-40}$ in the mouse brains, while the 5 mg dose reduced both Aβ$_{1-40}$ and Aβ$_{1-42}$. Neither dose significantly affected soluble Aβ species. The mechanism of insoluble Aβ removal was suggested, based on in-vitro experiments, to be galantamine's stimulation of α$_7$ nicotinic receptors on microglia, via the galantamine positive allosteric modulatory (PAM) site. (Takata et al, op cit) A shorter administration of galantamine, ten days at 2 mg/kg/day, did not reduce insoluble or soluble Aβ species in mice transgenic for a single, different Swedish APP mutation from that used by Takata et al, however it did significantly raise synaptophysin levels, suggesting a neurotrophic effect in the transgenic animals. (Unger et al, JPET 2006, 317, 30) In yet a third model of some aspects of AD, mice transgenic for an anti-NGF (nerve growth factor) antibody, deposit phosphorylated tau in the hippocampus, extracellular Aβ accumulations, and lose choline acetyltransferase (ChAT) in the nucleus basalis. (Capsoni et al, PNAS 2004, 99, 19, 12432) Galantamine, 3.5 mg/kg/day, restored ChAT activity, and decreased intracellular Aβ deposits after 15 days, with a similar result after 2 months' treatment. Amyloid deposition, therefore, appears to be reduced, and clearance increased, by the application of galantamine to transgenic animals or microglia in culture. This would be consistent with Wang et al's (J. Neurochem 2000 September 75(3); 1155-61) previous suggestion that $A\beta_{1-42}$ binds selectively to $\alpha_7$ nicotinic acetylcholine receptors.

In addition to effects on amyloid processing, galantamine can protect neurons against Aβ toxicity in cell culture. Primary rat cultured cortical neurons do not die when incubated with supraphysiological concentrations of $A\beta_{1-40}$ (10 nM) and $A\beta_{1-42}$ (1.0 nM), but toxicity is produced when a low dose of glutamate is added. (Kihara et al, Biochem Biophys Res Comm 2004, 325, 976) Galantamine 1.0 μM protects neurons against Aβ plus glutamate, while 0.1 μM, below the therapeutic range, has an intermediate effect which is not statistically significant. The galantamine rescue is not significantly reduced by mecarnylamine, a general nicotinic blocker, or by specific blockers $\alpha_7$ or $\alpha_4\beta_2$ receptors, but it is reversed by FK-1, an antibody to the galantamine allosteric site. Nicotine is also protective against Aβ plus glutamate toxicity and this is reversed by both $\alpha_7$ and $\alpha_4\beta_2$ blockade. Subthreshold doses of galantamine plus nicotine were also significantly effective together. A thousand-fold higher dose of $A\beta_{1-40}$, 10 μM, however is toxic to adrenal chromaffin and human neuroblastoma cells in culture. (Arias et al, Neuropharmacology 2004, 46, 103) Galantamine at clinical concentrations of 100 to 300 nM reduced $A\beta_{1-40}$-induced apoptosis, as well as that resulting from treatment with thapsigargin, a SERCA (sarcoendoplasmic reticulum calcium ATPase) inhibitor causing ER stress, a mechanism which is believed to contribute to neuronal degeneration in the AD brain. Galantamine's neuroprotective effect was blocked by α-bungarotoxin, a blocker of $\alpha_7$ nicotinic receptors, and it did not occur with tacrine, a cholinesterase inhibitor without nicotinic allosteric modulatory properties, suggesting that it occurred through $\alpha_7$ nAChRs. Galantamine thus appears to directly protect neurons from toxic pathways in the Alzheimer brain via enhancement of nicotinic transmission.

Amyloid plaques are believed to be associated with release of inflammatory cytokines which are believed to contribute to neurodegeneration in the Alzheimer brain. Galantamine exhibits anti-inflammatory properties in animals in vivo, as well as in microglia in culture. Galantamine, 1 mg/kg, administered prior to endotoxin, significantly reduces serum tumor necrosis factor (TNF). (Pavlov V A, Parrish W R, Rosas-Ballina M, et al, Brain acetylcholinesterase activity controls systemic cytokine levels through the cholinergic anti-inflammatory pathway, Brain Behav Immun 2009, 23, 41-45) This is mediated by central muscarinic synapses, in part through the vagus nerve and requires $\alpha_7$ nicotinic receptors, as it does not occur in $\alpha_7$ knockout mice. Survival is improved significantly only at 4 mg/kg.

Galantamine, 500 nM, has also been shown to reduce aggregation of 50 μM $A\beta_{1-40}$, a markedly supraphysiologic concentration. (Matharu et al, 0.1 Neural Sci 2009, 280, 49) Additionally, the release of $A\beta_{1-40}$ and $A\beta_{1-42}$ from neuroblastoma cells is decreased by 300 nM galantamine, as is the activity of β-secretase, which is involved in the production of those peptides, (Li et al, Exp Gerontol 2010, 45, 842).

From a study of these results, have concluded that galantamine thus exhibits preclinical evidence for the inhibition of the development of Alzheimer pathology by reducing Aβ deposition without lowering CSF Aβ and possibly aggregation as well as the neurotoxicity of several pathways which can lead to AD. Some of these effects are mediated by nicotinic receptors, mostly involving the galantamine positive allosteric modulatory site.

A two-year, randomized trial of galantamine (n=1028) and placebo (n=1023) was performed in mild-to-moderate AD patients to evaluate its safety, following a study in MCI patients halted for excess mortality in the galantamine group. Galantamine patients performed better than placebo patients on the MMSE at 6 months (−.28 for placebo; 0.15 for GAL; difference=0.43; p<0.001) and at 24 months (−2.14 for placebo; −1.41 for GAL; difference=0.73; p<0.001), a 34% difference, (Hager K, Baseman A S, Nye J S et al, Neuropsychiatric Disease and Treatment 2014, 10, 391-401) When patients receiving memantine, about 21% of the population, were removed from the analysis, galantamine patients deteriorated by 1.12 points at 24 months, compared to 2.15 points for placebo patients, a 48% reduction. In the overall population, galantamine's effect was reduced by including memantine patients, in whom galantamine was ineffective. Memantine is a potent blocker of nicotinic receptors. (Aracava Y, Periera E F R, Maelicke A, et al, Memantine blocks α7 nicotinic acetylcholine receptors more potently than N-methyl-D-aspartate receptors in rat hippocampal neurons, JPET 2005, 312, 11954206; Buisson B, Bertrand D, Open-channel blockers at the human α4β2 neuronal nicotinic acetylcholine receptor, Mol Pharmacol 1998, 53, 3, 555-563) Activities of daily living also declined less in galantamine than placebo patients as measured by the Disability Assessment in Dementia at 12 months (−6.50 for placebo vs −4.55 for GAL; difference=1.95; p=0.009) and at 24 months (−10.81 for placebo vs −8.16 for GAL; difference=2.65; p=0.002), a 24% difference. Mortality was 42% less in galantamine than in placebo patients, to the extent that the study was prematurely terminated and all patients were recommended to go onto galantamine treatment. Reduction of mortality, cognitive and functional loss all appeared to increase with time. Anatomic evidence compatible with a neuroprotective effect of galantamine was seen in a subpopulation of the two-year, placebo-controlled, randomized study in MCI patients. (Scheltens et al, presented at the International Conference on Alzheimer's Disease, Philadelphia, Pa., USA, Jul. 17-22, 2004), Global atrophy as assessed by serial MRIs was reduced 33% in galantamine as compared to placebo patients. Thus, galantamine may mitigate the progression of the Alzheimer process.

Of note, the magnitude of the reduction in cognitive decline in mild-to-moderate Alzheimer patients compares favorably to that of a combined calculation of mild AD patients from two solanezumab studies, and is greater than that of bapineuzumab. Galantamine's reduction in change in activities of daily living is greater than that in the other studies, and it preserved cortical volume, while patients receiving Aβ antibodies tended to lose cortical volume as compared to placebo patients.

Galantamine does not lower CSF Aβ, which implies that it does not lower interstitial fluid Aβ. (Nordberg et al, Curr Alz Res 2009, 6, 4) As discussed above, CSF Aβ is already reduced from normal in AD patients, and Aβ at physiological levels has important biological functions. The performance measures which are used to assess new treatments are likely the result of the activity of the healthy cells in the Alzheimer brain, not the dead and dying ones in the region of the plaques. The cells distant from plaques are the cells which are abnormally silent in the brain of the Alzheimer model transgenic mouse, (Busche et al, op cit) As these cells have a requirement of Aβ for learning and for their survival, anti-amyloid therapies which reduce soluble Aβ could deprive them of trophic and functional support, and impact cognitive and functional outcomes in treated patients.

Following excess mortalities in 2 studies of the use of galantamine to treat MCI, galantamine labeling was changed to include a warning against its use in MCI, and a commentary accompanying the study result publication recommended against its use. (Winblad et al, Neurology 2008; 70:2024-2035; Aisen P, Neurology 2008; 70:2020-2021) Within 30 days of stopping galantamine, there were 14 deaths in galantamine patients and 3 in placebo patients. The MCI studies were halted. A follow-up of mortality for the 24-month study period in all patients who were entered revealed 34 deaths in the galantamine group and 20 in the placebo group, RR [95% CI], 1.70 [1.00, 2.90], p=0.051. Deterioration on the CDR-SB was reduced in Study 1 at 24 months and tended to be reduced in Study 2. In one study, the effect at 24 months appeared greater than at 12 months, in the other study, it was the reverse. The reduced global atrophy, discussed above, occurred in a subset of Study 1 patients having repeated MRI scans.

The inconsistent results in the use of galantamine to treat patients with MCI over two years, unlike the persistent, substantial benefit seen in Alzheimer patients, may be a result of using 24 mg, the dose needed to treat a person with AD, in people who did not have the cholinergic deficit of Alzheimer's dementia. It is known that in moderate AD, 24 mg produces the best results, while in mild disease 16 mg per day is the best dose. (Aronson 5, Baelen B Y, Kavanagh S et al., Optimal dosing of galantamine in patients with mild or moderate Alzheimer's disease, Drugs Aging 2009, 26, 3, 231-239) Animal studies also show that the dose of cholinesterase inhibitor which is beneficial is correlated to the degree of cholinergic deficit, with higher and lower doses producing less benefit or even impairment. (Haroutunian V, Kanof P, Davis K L, Pharmacologic alleviation of cholinergic lesion induced memory impairment in mice, Life Sci 1986, 37, 945-952) As MCI patients do not have the cholinergic deficit seen even in mild AD, a galantamine dose which would be beneficial would be expected to have been less than 16 mg per day. Administering a dose of 24 mg would be expected to cause excess synaptic acetylcholine and to impair cognition at the C stage, resulting in counter-regulatory acetylcholinesterase secretion to restore optimal amounts of acetylcholine to the synapse. While a modest amount of acetylcholinesterase increase occurs in CSF in AD patients receiving galantamine, a greater amount may have occurred in MCI patients. However, the reduction in global atrophy in galantamine-treated MCI patients may be attributable to the drug's nicotinic activity, and may not have occurred at the lower dose optimal for a cognitive outcome. The 16 and 24 mg doses used, indicated for Alzheimer's disease, may have produced counter-regulatory changes in the cholinergic system needed to protect against excessive cholinergic activity, and may have impacted cognitive and functional outcomes. Genetically increased AChE levels can promote amyloid deposition. (Rees T, Hammond P I, Soreq H, et al, Acetylcholinesterase promotes beta-amyloid plaques in cerebral cortex, Neurobiol Aging 2003, 24, 777-787) A better approach to using the nicotinic activity of the galantamine molecule in patients who have not developed a substantial cholinergic deficit is to modify it to reduce its acetylcholinesterase activity.

Nicotinic mechanisms have been implicated in a vast variety of physiological and pathological processes, including, but not limited to, acute or chronic immune disease associated with organ transplantation; acute lung injury; addiction to, use of, or withdrawal from cocaine, nicotine, MDMA, cannabinoids, alcohol, opiates, or reduction of consumption; age related cognitive decline; AIDS dementia complex; allograft rejection; analgesia; Alzheimer's disease; antihelminthic effects; appetite suppression; attention deficit with or without hyperactivity; anxiety; arthritis; asthma; auditory sensitivity; autism; brain trauma; celiac disease; circadian rhythm alterations and jet lag; closed head injury; cognition deficit; cognition deficit associated with depression, bipolar disorder, stroke, brain trauma; cortical plasticity increase (e.g., post-stroke, for multitasking deficits, tinnitus); Crohn's disease; depression; Down's syndrome cognitive deficits; dyslexia; electro-convulsive therapy-induced memory impairment; endotoxemia and endotoxic shock; epilepsy; externalizing behaviors; heart failure; Huntington's disease; hyperkinesia; impulsive behavior; inflammatory bowel and bile diseases; insecticidal and antiparasitic effects; lack of circulation; lead blockage of post-synaptic nicotinic receptors; learning deficit; Lewy Body dementia; luteinizing-hormone releasing factor release; mania; manic depression; memory loss; mild cognitive impairment; multi-infarct dementia; multiple sclerosis; neuropathic pain; neuroprotection in Parkinson's, Alzheimer's diseases and cerebral hemorrhage; neurogenesis in the adult brain; ocular dominance plasticity; olivocerebellar ataxia; pain (including acute, chronic, inflammatory, postoperative, neuropathic); pancreatitis; Parkinson's disease (including cognition, l-dopa induced dyskinesias, and delay of onset); periodontitis; Pick's disease; postoperative ileus; post-stroke neuroprotection; pouchitis; psoriasis; Rett's syndrome; rheumatoid arthritis; rheumatoid spondylitis; sarcoidosis; schizophrenia (cognition, attentional functions, negative symptoms); sepsis; smoking cessation; social interactions; sudden infant death syndrome; tardive dyskinesia; tinnitus; toxic shock syndrome; Tourette's syndrome including tics; ulcerative colitis; urticaria; vascular dementia; vascularization of skin grafts and wound healing; ventilator-induced lung injury and visual acuity. Notwithstanding the long-standing need for treatments for many of these conditions, there is only one medication on the market, varenicline a nicotine partial agonist and it is used for smoking cessation.

SUMMARY OF THE PRESENT INVENTION

In broad concept, the present invention provides a method of treating certain persons who meet criteria for having a risk of developing dementia, and in particular Alzheimer's type dementia, before symptoms of dementia are observed with the objective of delaying the onset of such dementia.

From a first aspect the present invention provides a method for reducing the fall in Aβ42 in CSF of patients exhibiting a decreased Aβ42 level in CSF but not exhibiting signs of dementia which comprises administering thereto a therapeutically acceptable dose of a compound of an analog of (4aS,6R,8aS)-5,6,9,10,11,12-hexahydro-3-methoxy-11-methyl-4aH-[1]benzofuro[3a,3,2-ef][2]benzazepin-6-ol of the formula:

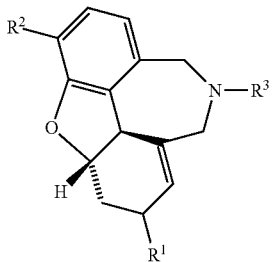

or a pharmaceutically acceptable salt thereof
wherein $R^1$ is carbamate, carbonate or carboxylate-group;
$R^2$ is an alkoxy, hydroxyl, hydrogen alkanoyloxy, benzoyloxy or substituted benzoyloxy, or carbamate group and
$R^3$ is hydrogen, alkyl of 1 to 10 carbon atoms, benzyl, cyclopropylmethyl group or a substituted or unsubstituted benzoyloxy group;
$R^1$ is typically an alkanoyloxy group of 2 to 10 carbon atoms, a benzoyloxy or substituted benzoyloxy group, a carbonate group of 1 to 10 carbon atoms or a carbamate group such as a mono alkyl or dialkyl or an aryl carbamate wherein the alkyl groups or aryl groups contain from 1 to 10 carbons. Mono alkyl carbamate groups of 2 to 8, for example 3 to 6 carbon atoms are particularly useful.

Carboxylate and carbamate groups are particularly useful.
Typically $R^2$ is alkoxy group of from one to six carbon atoms, a hydroxy group, hydrogen, an alkanoyloxy group of 2 to 10 carbon atoms, a benzoyloxy or substituted benzoyloxy group, a carbonate group of 1 to 10 carbon atoms or a carbamate group such as a mono alkyl or dialkyl or an aryl carbamate wherein the alkyl groups or aryl groups contain from 1 to 10 carbons;

Substituted benzoyloxy groups include from one to three substituents independently selected from hydrogen, hydroxyl, sulfhydryl, alkyl, aryl, aralkyl, alkoxy thioalkoxy, aryloxy, thioaryloxy, alkarloxy, thioalkaryloxy, nitro, amino, N-alkylamino, N-arylamino, N-alkarylamino, fluoro, chloro, bromo iodo and trifluoromethyl.

Commonly, $R^2$ and $R^3$ are methoxy and methyl respectively. Compounds as described above may form pharmaceutically acceptable salts which are suitable for use in the embodiments of the invention described below. Such salts include hydrochloride, hydrobromide, sulfate, nitrates, methane sulfonic, oxalate, malate, maleate and other known pharmaceutically acceptable acid salts.

As used herein, Aβ42 includes $A\beta_{1-42}$ and $A\beta_{x-42}$.
In this first embodiment of the invention, a therapeutic dose of the specified compound as described above is administered to patients having a CSF Aβ42 level of less than 225 pg/ml, and especially when the concentration is below 192 pg/ml as measured by the Luminex INNO-BIA AlzBio3 assay for example, or a corresponding value for a different assay, such as the Elisa INNO-BiA AlzBio3, for example in the range up to 650 pg/ml, in order to reduce the decline in CSF Aβ42. (Blennow et al, Trends in Pharmacological Sciences 2015, 36, 5, 297-309. An alternative measurement to CSF Aβ42 is the ratio of CSF $A\beta_{1-42}$ to tau or ptau. Bucchave et al (Arch Gen Psychiat 2012, 69, 1, 98) found that an Aβ42:ptau ratio<6.16 predicted the conversion of MCI patients to Alzheimer's dementia. References for the procedures and specific assays used are provided in the publication. Another biomarker ratio which can be used is a CSF Aβ42 to tau ratio below the discrimination line determined by Aβ42=240+1.18×tau, using the Innotest hTAU-Ag, Innogenetics (now Fujirebio), Ghent, Belgium sandwich ELISA, and the INNOTEST β-amyloid$_{(1-42)}$ sandwich ELISA (Innogenetics now Fujirebio, Ghent, Belgium, as depicted in FIG. 1 page 6, in Andreasen N et al, Neuroscience Letters 1999, 273, 5-8, or a similar ratio determined by other assays.

Thus, a CSF $A\beta_{1-42}$ to log-transformed P-tau$_{181p}$ ratio demonstrating the Alzheimer's signature as described by De Meyer et al (Arch Neurol 2010, 67(8), 949-956), or other biomarker ratio such as that described by Andreasen et al, op cit, or Bucchave et al, op cit, is capable of predicting the ultimate occurrence of Alzheimer's dementia, is also a criterion for treatment to delay the onset of dementia. The daily dose will be 0.1 to 100 mg, preferably 1-50 mg, or 2-10 mg, or 10-30 mg for example, given in a single dose, divided doses or a controlled release formulation. The daily dose can also be calculated based on weight, such as 0.001 to 0.15 mg/kg or 0.01 to 0.1 mg/kg.

In a second embodiment a therapeutic dose of the specified compound as described above is administered to patients who have been assessed by one or more standard tests (MMSE, ADAS-cog, Logical Memory Delayed Paragraph Recall, WAIS-R Digit Symbol Substitution, CDR-global, CDR-SB, NTB, logical memory IIA (delayed) and 1A (immediate), category fluency, delayed and immediate word-list recall, progressive matrices, ELSMEM, CogState, trailmaking, executive function, neuromotor speed, ADCS-ADL, DAD, and others) or a composite test composed of elements of these tests, to have impaired cognition or function, but not to be displaying dementia, and not having a condition not associated with Alzheimer pathology to which the impaired cognition or function can be solely attributed, so as to delay deterioration of cognition and/or function. The daily dose of a specified compound will be 0.1 to 100 mg, preferably 1-50 mg, or 2-10 mg or 10-30 mg for example, given in a single dose, divided doses or a controlled release formulation. The daily dose can also be calculated based on weight, such as 0.001 to 0.15 mg/kg or 0.01 to 0.1 mg/kg.

In third embodiment, a therapeutic dose of the specified compound will be administered to patients having medial temporal lobe, paralimbic, and/or temporoparietal lobe atrophy on structural MRI, or decreased fluorodeoxyglucose uptake in the temporoparietal cortices on PET scan, as described by Sperling et al, 2011, op cit, so as to delay deterioration. The daily dose of a specified compound will be 0.1 to 100 mg, preferably 1-50 mg, or 2-10 mg, or 10-30 mg for example, given in a single dose, divided doses or a controlled release formulation. The daily dose can also be calculated based on weight, such as 0.001 to 0.15 mg/kg or 0.01 to 0.1 mg/kg.

In a fourth embodiment, a therapeutic dose of the specified compound will be administered to patients whose CSF Aβ42 is decreasing, as determined by for example, a 1% drop per year when the lumbar puncture is done at the same time of day, a 10% drop from baseline, or decreases on two successive post-baseline samplings at least three months apart, in order to reduce the rate of decrease. The daily dose will be 0.1 to 100 mg, preferably 1-50 mg, or 2-10 mg; or 10-30 mg for example, given in a single dose, divided doses or a controlled release formulation. The daily dose can also be calculated based on weight, such as 0.001 to 0.15 mg/kg or 0.01 to 0.1 mg/kg.

In a fifth embodiment, a therapeutic dose of the specified compound may be used to increase the clearance of Aβ species from brain by administration of a daily dose from 0.1 to 100 mg, preferably 1-50 mg, or 2-10 mg, or 10-30 mg for example, given in a single dose, divided doses or a controlled release formulation. The daily dose can also be calculated based on weight, such as 0.001 to 0.15 mg/kg or 0.01 to 0.1 mg/kg.

In such an embodiment, β-amyloid will accumulate more slowly in brain than in untreated patients' brains. As noted above, such clearance may be determined by use of biomarkers in particular a ligand for amyloid plaques, visible on PET scan, such as Pittsburgh Compound B (PIB) Amyvid (florbetapir), Vizamyl (flutemetamol), Neuroseq(florbetaben) and $^{18}$F-NAV4694, and others which may be developed. Typically such treatments will be carried out on persons who do not exhibit symptoms of dementia, but who have Aβ accumulation in cortex, or levels of CSF Aβ42 less than 192 pg/ml, or declining at greater than 1% per year, or 10% from baseline, or decreases on two successive post-baseline samplings at least three months apart, as determined by the Luminex INNO-BIA AlzBio3 test kit, for example.

In a sixth embodiment, a therapeutic dose of the specified compound may be used in combination with a nicotinic agonist in order to inhibit plaque deposition or aid in removal of plaques of Aβ, prevent the decrease of Aβ42 in CSF or cause an increase in Aβ42 in CSF, delay progression to Alzheimer's disease dementia, or reduce the loss of cognition and/or activities of daily living. In such an embodiment, a specified compound, the daily dose will be 0.1 to 100 mg, preferably 1-50 mg, or 2-10 mg, or 10-30 mg for example, given in a single dose, divided doses or a controlled release formulation. The daily dose can also be calculated based on weight, such as 0.001 to 0.15 mg/kg or 0.01 to 0.1 mg/kg.

Suitable agonists include nicotine, varenicline, cytisine, dianicline, ABT-594, DMXB-A, TC 1734, ABT 107, Mem 3454(RG3487), ABT 894, 5-I A-85380, GTS 21, A-582941, EVP 6124, SKL A4R, AZD 1446, TC 5619, AZD 0328, and the like.

In a seventh embodiment, a therapeutic dose of the specified compound is administered to a patient who has been determined to have the ApoE4 isoform of Apolipoprotein E but who is not exhibiting signs of dementia in an amount sufficient to inhibit plaque deposition or aid in removal of plaques of Aβ, or to reduce the fall in CSF Aβ42, or prevent progression of cognitive and/or functional decline, or prevent progression to Alzheimer's dementia. In such embodiment, the daily dose of a specified compound will be 0.1 to 100 mg, preferably 1-50 mg, or 2-10 mg, or 10-30 mg for example, given in a single dose, divided doses or a controlled release formulation. The daily dose can also be calculated based on weight, such as 0.001 to 0.15 mg/kg or 0.01 to 0.1 mg/kg.

In an eighth embodiment individuals with Down's syndrome are administered a therapeutic dose of the specified compound as described above to inhibit β-amyloid plaque deposition in brain, or decrease the fall in CSF Aβ42, or decrease the loss of cognitive and functional abilities, or prevent progression to Alzheimer's dementia. In such embodiment, the daily dose of the specified compound will be 0.1 to 100 mg, preferably 1-50 mg, or 2-10 mg, or 10-30 mg for example, given in a single dose, divided doses or a controlled release formulation. The daily dose can also be calculated based on weight, such as 0.001 to 0.15 mg/kg or 0.01 to 0.1 mg/kg.

In a ninth embodiment a therapeutic dose of the specified compound is administered to a patient who has been determined to carry a fully-penetrant mutation which causes Alzheimer's dementia. In such an embodiment, the daily dose of a specified compound will be 0.1 to 100 mg, preferably 1-50 mg, or 2-10 mg, or 10-30 mg for example, given in a single dose, divided doses or a controlled release formulation. The daily dose can also be calculated based on weight, such as 0.001 to 0.15 mg/kg or 0.01 to 0.1 mg/kg.

Determination of the presence of such mutation may be determined by genetic testing.

In a tenth embodiment, a therapeutic dose of the specified compound is co-administered to a patient who has not developed Alzheimer's dementia but who has been determined to have a potential for Alzheimer's disease based on lowered or falling CSF Aβ42 as described in the first embodiment, reduced cognitive or functioning ability as described in the second embodiment, MRI or fluorodeoxyglucose PET Alzheimer-type changes as described in the third embodiment, decrease of Aβ42 CSF as described in the fourth embodiment, increased Aβ amyloid in brain as described in the fifth embodiment or presence of the ApoE4 isoform of Apolipoprotein E as described in the seventh embodiment or who have a penetrant mutation known to correlate with Alzheimer's dementia as described in the ninth embodiment, with agents such as solanezumab, aducanumab or gantenerumab, which promote clearance by administering Aβ antibodies or stimulating antibody production, or binding or resulting in binding to Aβ species, in order to enhance clearance of Aβ, cognitive and/or functional abilities, or retard conversion to Alzheimer's dementia. In such an embodiment, the daily dose of a specified compound will be 0.1 to 100 mg, preferably 1-50 mg, or 2-10 mg, or 10-30 mg for example, given in a single dose, divided doses or a controlled release formulation. The daily dose can also be calculated based on weight, such as 0.001 to 0.15 mg/kg or 0.01 to 0.1 mg/kg.

In an eleventh embodiment, a therapeutic dose of the specified compound will be given to patients who have cognitive complaints or subtle deficiencies, who do not have Alzheimer's dementia or other diseases as a sole cause of their cognitive issues, in order to improve performance, or to slow decline, on tests such as the MMSE, ADAS-cog, Logical Memory Delayed Paragraph Recall, WAIS-R Digit Symbol Substitution, CDR-global, CDR-SB, NTB, logical memory IIA (delayed) and 1A (immediate), category fluency, delayed and immediate word-list recall, progressive matrices, ELSMEM, CogState, trailmaking, executive function, neuromotor speed, ADCS-ADL, DAD, and others, preferably the CDR-SB, category fluency and ADCS-ADL, or a composite of questions from the MMSE, ADAS-cog, paragraph recall, digit-symbol substitution and NTB or other tests. The daily dose will be 0.1 to 100 mg, preferably 1-50 mg, or 2-10 mg, or 10-30 mg for example, given in a single dose, divided doses or a controlled release formulation. The daily dose can also be calculated based on weight, such as 0.001 to 0.15 mg/kg or 0.01 to 0.1 mg/kg.

When referring to a person who has not yet developed dementia or Alzheimer's dementia, I mean a person who would not have been diagnosed as suffering from probable Alzheimer's disease according to the NINCDS-ADRDA, or McKhann criteria published in 1984, or definite Alzheimer's disease if there is tissue from biopsy or an autopsy was done on a deceased person. Typically, a person is considered to have dementia if he or she has a score of 26 or less on the Minimental State Exam. (Folstein, M F; Folstein, S E; McHugh, P R (1975). "Mini-mental state". A practical method for grading the cognitive state of patients for the clinician, Journal of Psychiatric Research 12 (3)): Standard dementia cut-offs for the MMSE are less than or equal to 26, and for the CDR-SB, 1.0. However, it is important that a cutoff for dementia take into account such factors as cognitive reserve, age, education, etc. In a sample of U.S. adults selected from census data, the median MMSE was 29 for individuals with 9 years of schooling, 26 for 5 to 8 years of schooling, and 22 for people with 4 or fewer years of education. (Crum R, et al, AMA 1998, 269, 2386-2391). In a Finnish population of 511 subjects 75 to 85 years old, 446 of whom were non-demented based on their CDR scores, the MMSE scores were corrected according to age and education, which correlated with social group. The MMSE cutpoints for dementia, in low and high education groups respectively, were 25 and 26 in 75-year olds, 23 and 26 in 80-year olds, and 22 and 23 in 85-year old people. (Ylikoski R et al, Acta Neurol Scand 1992, 85, 391-396) Thus, demographic factors employing the best available data may be taken into account in determining the presence of dementia.

As noted above, Aβ performs important functions in brain when present in the right form, in the right locations and at the right concentration. However, oligomerization and aggregation of Aβ lead to toxicity and reduction of Aβ42 concentrations in regions where its presence is desired. Compounds of the present invention should therefore be utilized in amounts that optimizes their concentration in brain to achieve the removal of oligomers without significant adverse impact on concentrations of Aβ monomer. Concentrations in brain of from 0.2 to 1.5 µM of an analog of (4aS,6R,8aS)-5,6,9,10,11,12-hexahydro-3-methoxy-11-methyl-4aH-[1]benzofuro[3a,3,2-ef][2]benzazepin-6-ol, for example 0.5 to 1.0 µm, such as about 1 µM seem best suited for this purpose. As discussed below a therapeutic dose is one that achieves this concentration in brain.

BRIEF DESCRIPTION OF THE DRAWINGS

The file of this patent contains at least one drawing or photograph executed in color. Copies of this patent with color drawing(s) or photograph(s) will be provided by the Patent and Trademark Office upon request and payment of necessary fee.

FIG. 1 shows the current concept of the course of biomarker changes preceding clinical Alzheimer's disease (Sperling et al Alzheimer's and Dementia 2011, 7, 280).

DETAILED DESCRIPTION OF THE INVENTION

Figure 2:
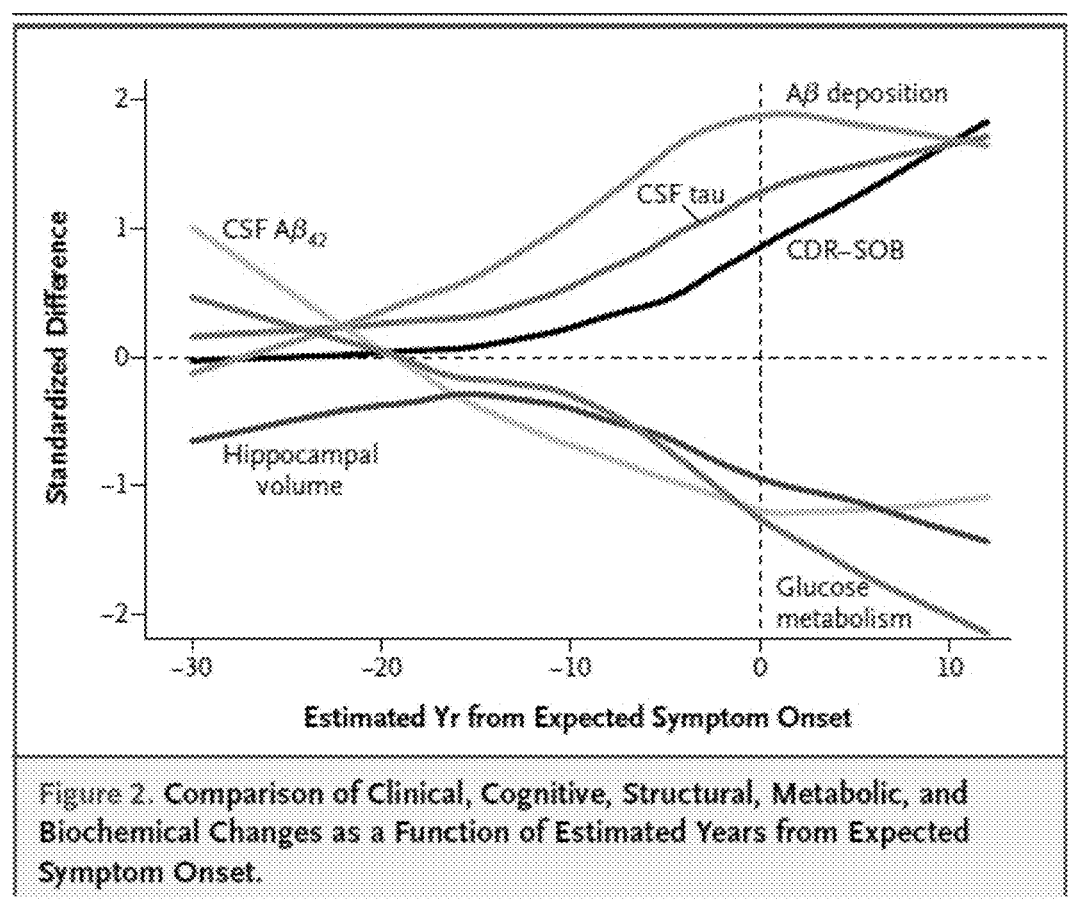
FIG. 2 shows the course of biomarker changes in patients with monogenic Alzheimer's disease (AD) (Bateman et al, op cit).

One particularly useful compound is the n-butylcarbamate derivative (4aS,6R,8aS)-5,6,9,10,11,12-hexahydro-3-methoxy-11-methyl-4aH-[1]benzofuro[3a,3,2-ef][2]benzazepin-6-ol (SDL 11349) having the structure:

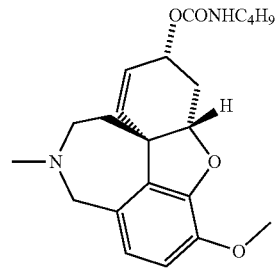

The $IC_{50}$ for acetylcholinesterase inhibition for SDL 11349 is $10.9 \times 10^{-7}$M as compared to $3.97 \times 10^{-7}$M for galantamine.

This compound was first described in Han et al as a cholinesterase inhibitor in Bioorg. & Medicinal Chemistry Letters 1, 11 579-580 (1991).

The pathways by which galantamine cleared Aβ, and protected neurons against Aβ, glutamate and SERCA inhibition toxicity, can be activated by analogs which preserve the nicotinic positive allosteric modulatory properties of the molecule, while markedly reducing cholinesterase inhibition. Galantamine butylcarbarnate has about 36% of the enzymatic activity of galantamine.

Primary cultured rat neurons can be depolarized by the application of 1.5 mM choline. (Popa et al, J Mol Netirosci 2006, 30, 27). This is mediated by $\alpha_7$ nicotinic receptors, as it could be blocked by methyllyaconitine and α-bungarotoxin, Galantamine n-butylcarbamate, 1 µM, enhanced the depolarization caused by choline (15.9±2.1%). This was not significantly different from the effect of galantamine at the same concentration (20.6±4.2%). The enhancement produced by the n-butylcarbamate was blocked by the antibody to the galantamine recognition site on nicotinic receptors, FK-1, indicating that it was mediated by the galantamine positive allosteric modulatory site. Galantamine n-butylcarbamate is thus a positive allosteric modulator at the galantamine site, with an effect similar to that of galantamine.

The butylcarbamate differed from galantamine in adverse effects. (Han et al, Eur J Med Chem 1992, 27, 673) Decreased motility which appeared at 5 mg/kg in galantamine-treated animals was not observed up to 30 mg/kg of the analog. At doses of 50-100 mg/kg of the n-butylcarbamate, mice were wobbly and off-balance with rapid heart rate still present at 4 hours, but were recovered at 24 hours. There was no lethality up to 100 mg/kg. The LD50 of galantamine is 10 mg/kg. Mice injected IP with 10, 15 and 20 mg/kg galantamine develop seizures at an average of 8, 6 and 4 minutes respectively. (Fonck et al, J Neurosci 2003, 3, 7, 2582)

Galantamine n-butylcarbarmate is predicted to have 80% oral bioavailability, based on in vitro permeability of a layer of CaCo-2 cells, derived from a human colorectal carcinoma, as shown below.

| Client ID | test conc (μM) | Assay duration (hr) | mean A->B $P_{app}^{a}$ ($10^{-6}$ cm s$^{-1}$) | comment |
|---|---|---|---|---|
| Ranitidine | 50 | 2 | 1.1 | low permeability control |
| Warfarin | 50 | 9 | 34.7 | high permeability control |
| Galanthamine Carbamate | 50 | 2 | 20.8 | |

$^{a}$ Apparent permeability

In an in-vitro preparation of liver microsomes, the half-life of galantamine n-butylcarbamate was greater than 60 minutes.

As shown below, this suggests that the compound is not metabolized to a substantial degree in the liver.

| Client ID | test conc (μM) | test species | NADPH-dependent $CL_{int}^{a}$ (μl min$^{-1}$ mg$^{-1}$) | NADPH-dependent $T_{1/2}^{b}$ (min) | NADPH-free $CL_{int}^{a}$ (μl min$^{-1}$ mg$^{-1}$) | NADPH-free $T_{1/2}^{b}$ (min) | comment |
|---|---|---|---|---|---|---|---|
| Verapamil | 5.0 | Mouse | 99.8 | 23.2 | 1.8 | >60 | metabolized control |
| Warfarin | 5.0 | Mouse | >1000 | >60 | 0.0 | >60 | non-metabolized control |
| Galanthamine HBr | 5.0 | Mouse | 0.0 | >60 | 0.0 | >60 | |
| Galanthamine Carbamate | 5.0 | Mouse | 23.5 | 98.2 | 0.0 | >60 | |

$^{a}$Microsomal Intrinsic Clearance
$^{b}$Half-life

Figure 3:
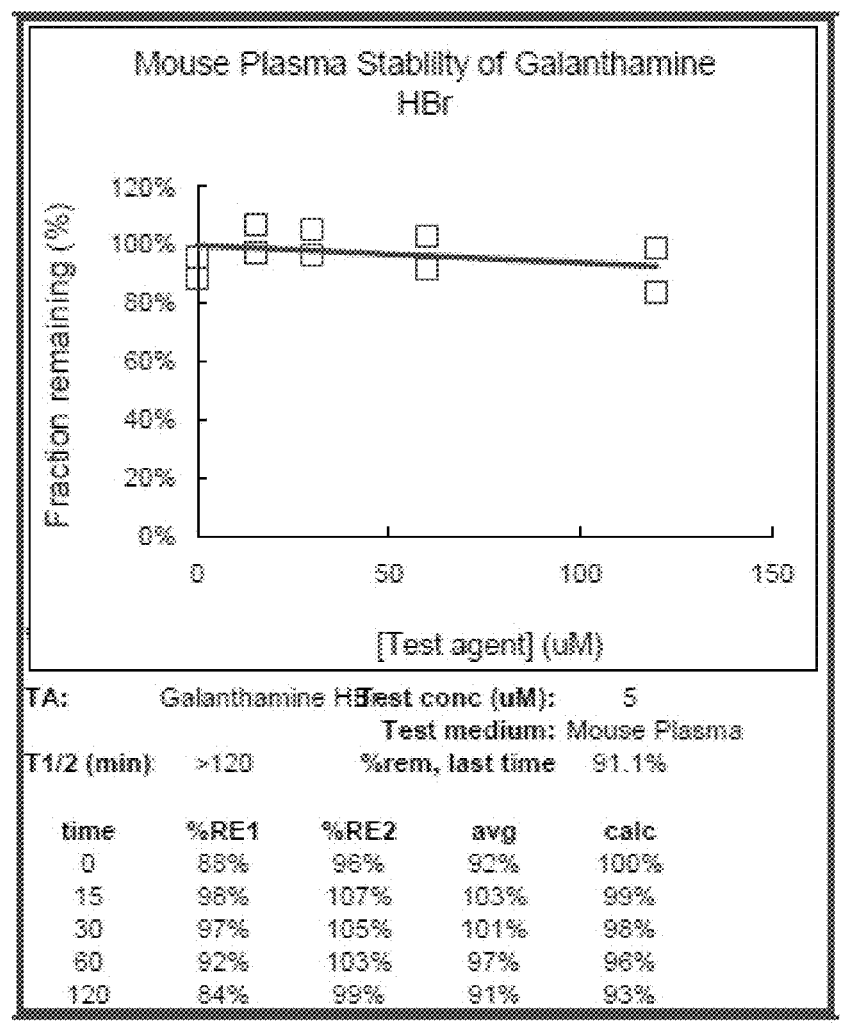
FIG. 3 shows the stability of galantamine in mouse plasma over two hours.
Figure 4:
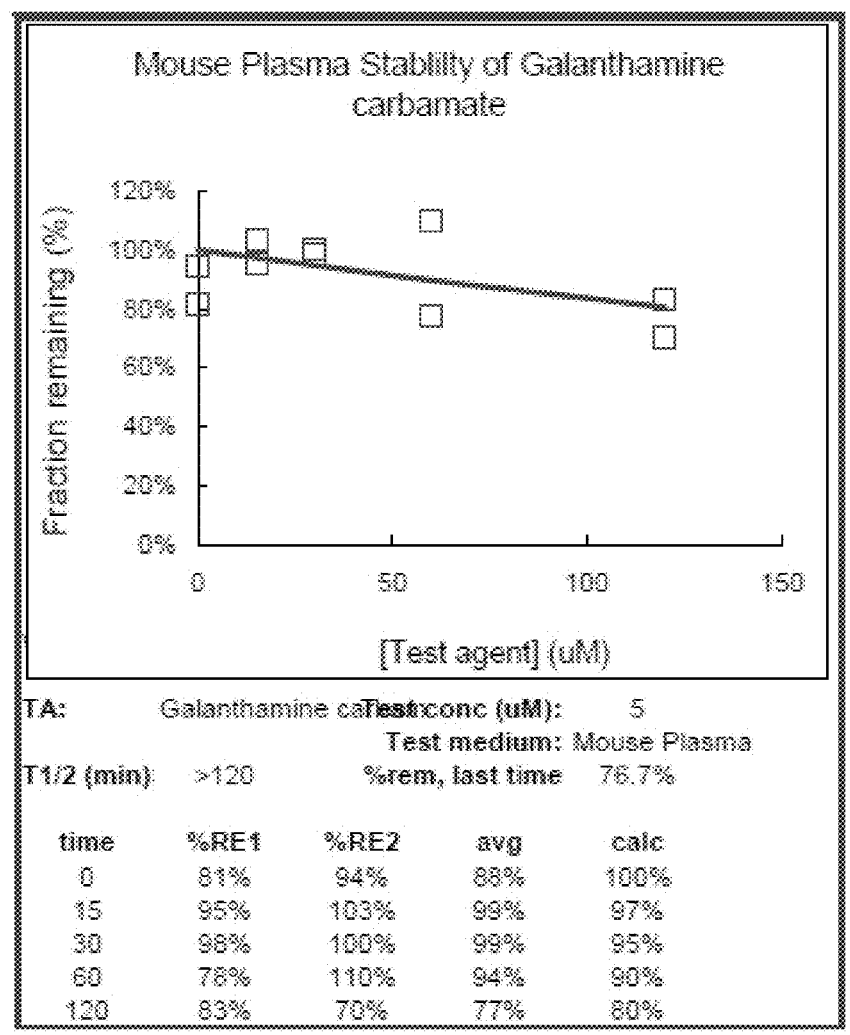
FIG. 4 shows the stability of galantamine n-butylcarbamate (SDL 11349) in mouse plasma over two hours.

Galantamine n-butylcarbamate is stable for greater than two hours in mouse plasma. Concentrations at two hours are slightly lower than those of galantamine which has a plasma half-life of about 7 hours in human patients. The mouse plasma data are shown in FIGS. 3 and 4. The pharmacokinetic data were produced by Apredica, 313 Pleasant St, Watertown Mass. 02472.

Figure 5:
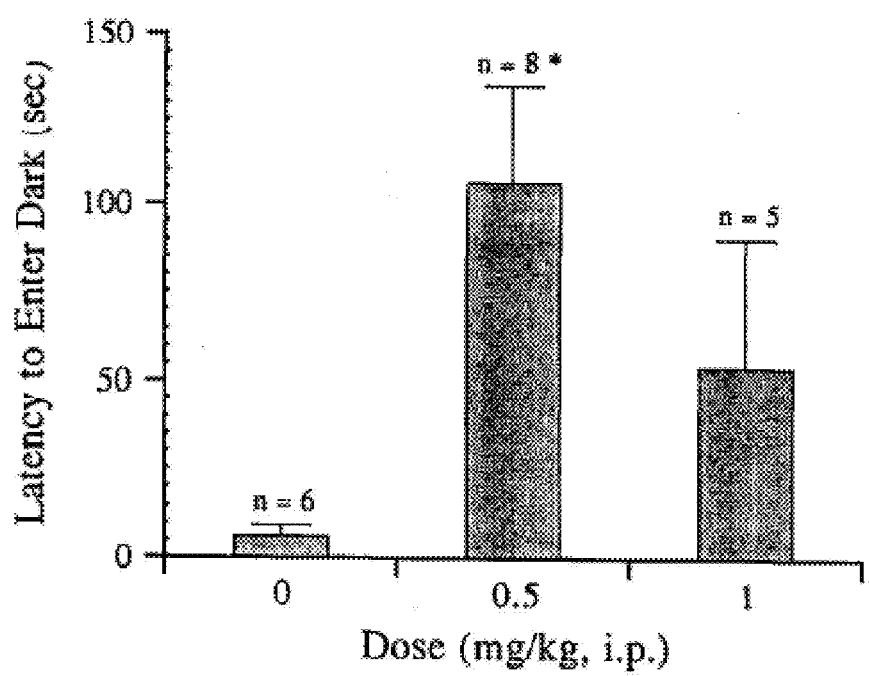
FIG. 5 shows the effect of doses of galantamine n-butylcarbamate (SDL 11349) in passive avoidance in the nBM mouse (Han et al, 1992).

Mice with lesions of the nucleus basalis magnocellularis (nBm) have poor memory for the fact that if they cross from a lighted compartment into a dark one, which they prefer, they will receive a shock through the floor grid. When given galantamine n-butylcarbamate during training, mice will remain in the lighted compartment about 100 seconds longer than when given saline. (Han et al, 1992, op cit) As shown in FIG. 5, the best dose for this memory enhancement is 0.5 mg/kg.

A similar effect is seen with galantamine. However, optimal performance is an increase of about 125 seconds, and the best dose is 3 mg/kg, 6× that of the n-butylcarbamate.

Figure 6:
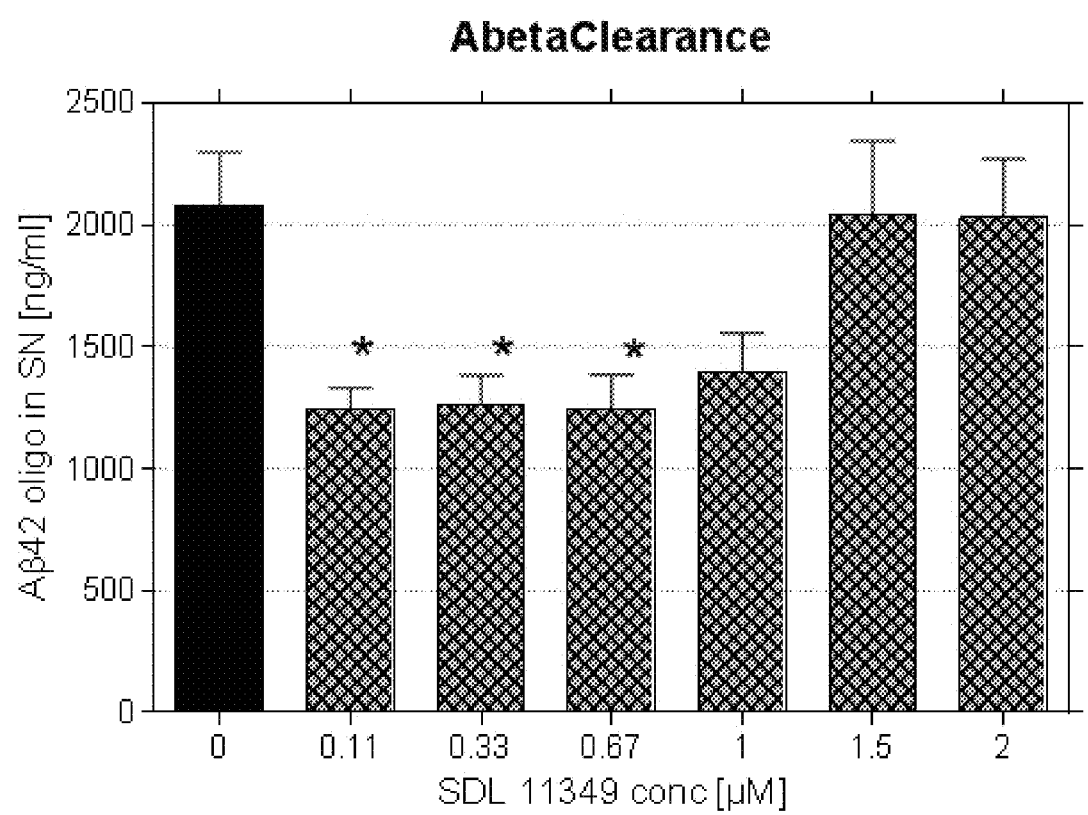
FIG. 6 shows the effect of SDL 11349 to increase clearance of Abeta 1-42 oligomers in a microglial Bv-2 cell culture.
Figure 7:
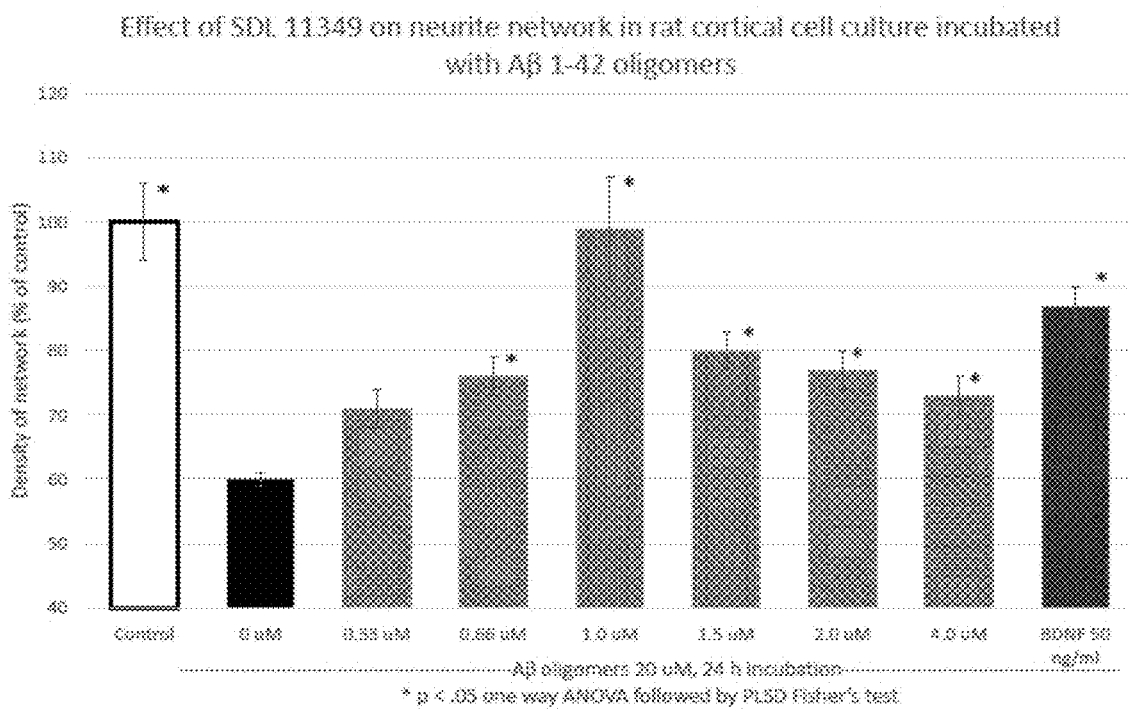
FIG. 7 shows the effect of SDL 11349 to prevent destruction of the neurite network by Abeta 1-42 oligomers in a cortical cell culture.
Figure 8:
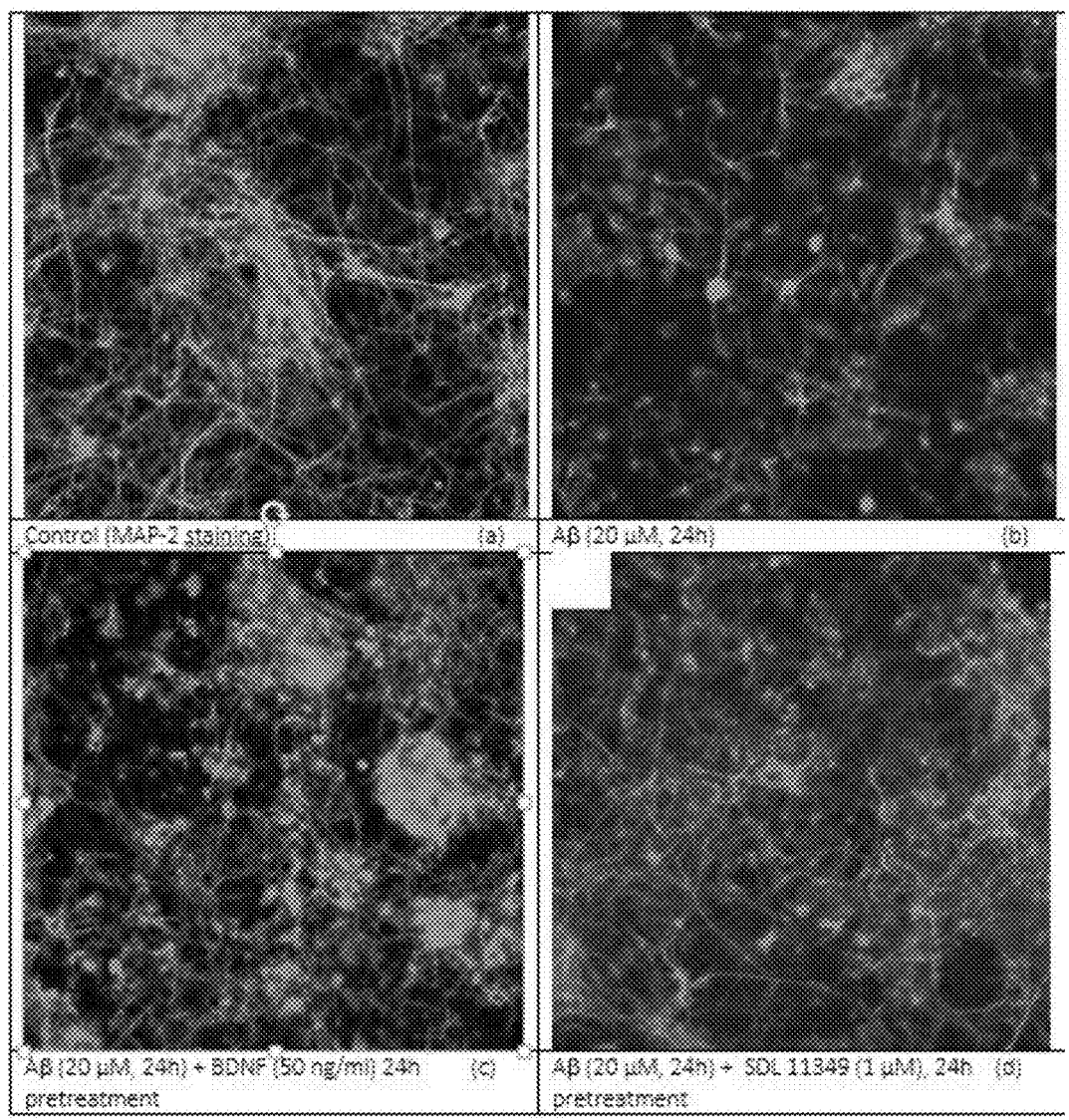
FIG. 8 shows photographs of the neurite network in a cortical cell culture: control, Abeta 1-42, and Abeta 1-42 with BDNF or SDL 11349.

In summary, SDL 11349 based on animal and in-vitro studies, appears to be well tolerated, safe, orally bioavailable, stable in plasma, and effective in enhancing learning at lower doses than galantamine. It enhances neuronal electrophysiological activity via the galantamine positive allosteric modulatory site on nicotinic receptors. It substantially enhances the clearance of toxic Aβ42 oligomers by microglial cells, to a degree greater than the clearance deficit identified in late onset AD patients (FIG. 6). Furthermore, it can prevent Aβ42 oligomer-induced loss of dendrites, a characteristic finding in the Alzheimer brain, a protective effect comparable to that of the "gold standard", BDNF (brain-derived neurotrophic factor), (FIG. 7) This is easily appreciated from the photomicrographs (FIG. 8). Dendritic spines are decreased in the Alzheimer brain (Gruntzendler et al, op cit). These spines, particularly mature ones with more frequent large heads, are significantly increased by subchronic SDL 11349 treatment in young adult mice in the stratum radiatum of CAL This area is affected early in AD and its width correlates with cognitive functions. (Kerchner G A et al, Neuroimage 2012, 63(1), 194-202) (FIGS. 9-11) Thus, SDL 11349 increases clearance of AB42 oligomers to a substantial extent, while protecting against the toxicity of remaining oligomers, and has trophic effects in one of the earliest affected areas in AD. The present invention utilizes concentrations in brain of from about 0.05-1.8 μM, more commonly 0.2 to 1.5 μM for example about 0.5-1.0 μM of an analog of (4aS,6R,8aS)-5,6,9,10,11,12-hexahydro-3-methoxy-11-methyl-4aH-[1]benzofuro[3a,3,2-ef][2]benzazepin-6-ol. Determination of suitable dose ranges for individual compounds can be effected by assessing the concentration of the analog which promotes Aβ oligomer clearance in vitro, and to temper that with the concentration which preserves the neurite network from injury by remaining oligomers. The analog is then administered to experimental animals to determine plasma and brain concentrations, and the plasma concentration which is associated with an effective brain concentration is applied to human subjects. Several concentrations will typically be tried in human subjects, with measurement of Aβ species in brain or Aβ42 in CSF, and clinical outcomes.

Compositions suitable for use in treatments according to the invention are typically suitable for oral administration such as tablets, capsules, or lozenges containing from 0.1 to 40 mg, of the active compound depending upon the activity and half-life of the compound. Compositions using SDL 11349 will typically contain, for example, in the range 0.5 to 10 mg, or 1 to 8 mg per dose.

Oral dosage forms may be sustained dosage formulations in which the particles of the active compound are coated so as to delay release into the blood stream for example by coating with a pharmaceutically acceptable polymer that is dissolved in gastric juices such as polyvinyl pyrrolidone and then sizing the particles and incorporating specific ratios of particles of particular sizes into a tablet, capsule or lozenge so that particles having different degrees of thickness of coating are released at different times, or using a controlled-release device which employs osmosis, for example. In the present case, the coating or delayed technique will desirably result in most of the active compound being released within twelve hours of administration. Alternative means of application may include for example transdermal patches in which case the objective is to provide administration of a dosage at a rate of 0.01 to 10 mg per hour.

Other dosage forms may be used if desired. For example nasal or parenteral, including dosage formulations to assist passage of the blood-brain barrier.

For the purpose of nasal or parenteral therapeutic administration, the active compounds of the invention may be incorporated into a solution or suspension. These preparations typically contain at least 0.1% of active compound, for example between 0.5 and about 30% of the weight of the solution or suspension. Preferred compositions and preparations according to the present inventions are prepared so that a nasal or parenteral dosage unit contains between 0.1 to 10 milligrams of active compound.

The solutions or suspensions may also include the following components: a sterile diluent such as water for injection, saline solution, fixed oils, polyethylene glycols, glycerine, propylene glycol or other synthetic solvents; antibacterial agents, such as benzyl alcohol or methyl parabens; antioxidants such as ascorbic acid or sodium bisulfite; chelating agents such as ethylene-diamine tetraacetic acid; buffers such as acetates; citrates or phosphates and agents for the adjustment of tonicity such as sodium chloride or dextrose. Parenteral multiple dose vials may be of glass or plastic.

Typical dosage rates in administration of the active ingredients depend on the nature of the compound that is used and in intravenous administration are in the range of 0.01 to 2.0 mg per day and per kilogram of body weight based on the physical condition and other medications of the patient.

Liquid formulations for nasal or intra-cerebroventricular administration at a concentration of 0.1 to 5 mg of active ingredient/ml. The compounds according to the invention can also be administered by a transdermal system, in which 0.1 to 10 mg/day is released. A transdermal dosage system may consist of a storage layer that contains 0.1 to 30 mg of the active substance as a free base or salt, in case together with a penetration accelerator, e.g., dimethyl sulfoxide, or a carboxylic acid, e.g., octanoic acid, and a polyacrylate, e.g., hexylacrylate/vinyl acetate/acrylic acid copolymer including softeners, e.g., isopropylmyristate. As a covering, an active ingredient-impermeable outside layer, e.g., a metal-coated, siliconized polyethylene patch with a thickness of, for example, 0.35 mm, can be used. To produce an adhesive layer, e.g., a dimethylamino-methacrylate/methacrylate copolymer in an organic solvent can be used.

The determination of a particular dose for any given patient will be a matter for the judgment of the physician treating the patient. However, when using SDL11349, these will be in the range of from 1.0 to 10 mg or 2 to 8 mg per day to achieve a concentration in brain in the range 0.4-1.2 µM.

Some compounds of use in the present invention are acetyl cholinesterase inhibitors. For some users of these drugs, inhibition of acetylcholinesterase may lead to excess mental activity during periods of intended sleep and lead to insomnia. For such persons, a dosage regime should be chosen to avoid significant levels of active compounds in the brain during periods of intended sleep. The half-life of the compounds of the present invention in the body is typically less than 12 hours and may be as low as six hours. Avoidance of significant concentrations of active compound during periods of intended sleep can therefore be achieved by avoiding taking drug in the evening, for example taking a daily dose divided into two, three or four units to be taken throughout the day, typically to be taken at meal times. Alternatively a delayed or sustained drug release formulation may be used.

For other users, sleep disorders may not be a problem and there may be benefit in maintaining levels of (4aS,6R,8aS)-5,6,9,10,11,12-hexahydro-3-methoxy-11-methyl-4aH-[1]benzofuro[3a,3,2-ef][2]benzazepin-6-ol analogs during sleep to assist in clearance of β-amyloid species from brain through the glymphatic system.

For an individual patient, suitable dosages may be determined by starting with a low daily dose such as 0.1 mg, or 1 to 2 mg, and increasing if there is insufficient response. The amounts of active compounds required by the present invention are those that will promote removal of or retard accumulation of Aβ deposits in cortex while reducing the lowering of CSF Aβ42. Depending on the relative efficacy of the compound as a cholinesterase inhibitor and a nicotinic stimulator, this may be lower than the dose required to treat dementia associated with Alzheimer's disease where acetylcholinesterase inhibition is an important requirement. This property is not a desirable factor in choosing a dose for the present invention.

Treatments according to the first and second embodiments of the invention require a determination of levels of $A\beta_{1-42}$ or $A\beta_{x-42}$ monomer, referred to as Aβ42, in the CSF, or measures reflecting β-amyloid deposits in cortex. This can be effected by standard methods such as lumbar puncture and PET scanning with ligands for β-amyloid such as Pittsburgh Compound B (PIB), Amyvid (florbetapir), Visamyl (flumetamol), Neuroseq (florbetaben)$^{18}$F-NAV4694 or others which may be developed. The determination of the levels of CSF Aβ42 at which treatment should be commenced will depend upon a variety of factors such as age, education, ApoE4 status, diabetes, genes which cause AD and others. The cutoff for Aβ42 concentration is based on CSF Aβ42 concentrations in CSF indicating Aβ deposition in brain, and a similar value separating healthy elderly from Alzheimer's disease patients. (Weigand et al, op cit; De Meyer et al, op cit) Typically, however, treatment will be commenced if CSF Aβ42 levels fall below 225 pg/ml, for example, below 192 pg/ml as determined using the INNO-BIA AlzBio3 test kit Luminex assay or 450-650 pg/ml, using the Innotest β-amyloid$_{(1-42)}$ ELISA assay, depending on the PET tracer and cortical and reference regions, or have been dropping by more than 1% per year, 10% since the baseline measurement, or have fallen on two consecutive post-baseline measurements, with at least 3 month intervals. A summary of currently available CSF Aβ42 levels corresponding the cortical Aβ deposition is available in Blennow et al, Trends in Pharmacological Sciences, 2015, 36, 5, 297, Table 2. Standardization efforts within the Alzheimer research community are underway for this measurement.

Treatment according to the third embodiment of the invention may involve volumetric MRI scanning or determination of fluorodeoxyglucose uptake by PET scanning, as noted by Sperling et al., op cit 2011.

Treatment according to the sixth embodiment of the invention involves administration of nicotine agonists such as EVP 6124, DMXB-A, AZD 1446, ABT 894, or others mentioned above together with one of (4aS,6R,8aS)-5,6,9,10,11,12-hexahydro-3-methoxy-11-methyl-4aH-[1]benzofuro[3a,3,2-ef][2]benzazepin-6-ol's analogs as specified above. The agonists assist in clearance of Aβ from plaque and so establishment of useful levels where required is by beginning low and increasing the dose until a response is seen in PET scanning for amyloid, or CSF Aβ consisting of a slower progression of abnormality. The combination of a (4aS,6R,8aS)-5,6,9,10,11,12-hexahydro-3-methoxy-11-methyl-4aH-[1]benzofuro[3a,3,2-ef][2]benzazepin-6-ol analog and a nicotinic agonist may cause cardiac side effects and extreme caution should be used with this combination. Typically the daily dose of (4aS,6R,8aS)-5,6,9,10,11,12-hexahydro-3-methoxy-11-methyl-4aH-[1]benzofuro[3a,3,2-ef][2]benzazepin-6-ol analog and agonists will be will be 0.1 to 100 mg, preferably 1-50 mg, or 2-10 mg, or 10-30 mg for example, given in a single dose, divided doses or a controlled release formulation. The daily dose can also be calculated based on weight, such as 0.001 to 0.15 mg/kg or 0.01 to 0.1 mg/kg and 0.5 to 50 mg for the agonists. The actual dosages of each will be determined by following amyloid levels in brain and Aβ42 in CSF and will typically be in the range of 0.2 mg to 100 mg for a (4aS,6R,8aS)-5,6,9,10,11,12-hexahydro-3-methoxy-11-methyl-4aH-[1]benzofuro[3a,3,2-ef][2]benzazepin-6-ol analog, preferably 2-10 mg, or 1-50 mg and from 0.5 mg to 50 mg for the agonist, preferably 2-30 mg.

Treatment according to the seventh embodiment of the invention requires determination of whether a patient has the ApoE4 isoform of Apolipoprotein E. This may be done by genetic testing. If a patient is found to fall into this category, suitable dosage levels may be determined in the same manner as for the first and second embodiments.

Treatment according to the eighth embodiment, Down's syndrome, would follow the guidelines of amyloid deposition as described with respect to the sixth embodiment and CSF Aβ42 as described with respect to the first and second embodiments.

(4aS,6R,8aS)-5,6,9,10,11,12-hexahydro-3-methoxy-11-methyl-4aH-[1]benzofuro[3a,3,2-ef][2]benzazepin-6-ol and its analogs for use according to the present invention share the same contraindications as other cholinergic drugs. Thus care should be taken before using the present invention on pre-pubertal children and patients who suffer for example from asthma, epilepsy, bradycardia, heart block, hemorrhagic ulcer disease. Furthermore, animal studies have shown that cholinergic drugs may result in overstimulation of the uterus and ovaries in premenopausal women.

The present invention is illustrated by the following examples.

Oligomer Clearance Measurement
Procedures

Abeta oligomers were prepared using beta-amyioid (1-42) from American Peptide (Product #62-0-80). One aliquot was dissolved in an adequate volume of TBS (50 mM Tris-Buffer, 150 mM NaCl, pH=7.4) to achieve a final concentration of 1.7 mg/ml (corresponding to 340 μM). The solution was sonicated for 2 minutes and then diluted 1:2 in water to obtain a final concentration of 170 μM. Next, the Abeta was allowed to aggregate at 4'C for 48 hours. Prior to application, the solution was sonicated for another minute.

Bv-2 microglial cells were kept in culture medium (DMEM medium, 10% FBS, 2 mM glutamine, 1% Penc/Strep) until 80-90% confluency. Cells were maintained at 37° C., 95% humidity and 5% $CO_2$. Afterwards, cells were seeded in culture medium on 24-well plates at a cell density of $1 \times 10^5$ cells per well. After 24 h, the medium was exchanged for the treatment medium (DMEM medium, 5% FBS, 2 mM glutamine). Cells were treated with different concentrations of SDL 11349 as depicted in FIG. 6 for 24 h before oligomer application. Oligomerized Aβ1-42 (10 μM) was applied to the cells for 6 h. Afterwards the cell supernatant (medium) was collected. The medium was separated by affinity (removing monomers) and the oligomers not phagocytosed were disaggregated by HFIP treatment and measured by MSD. (MSD® 96-well MULTI-SPOT®6E10 Abeta Triplex Assay (Mesoscale Discovery)

The immune assay was carried out according to the manual and plates were read on the Sector Imager (MSD). Analyte levels were evaluated according to adequate Aβ peptide standards (MSD). Experiments were carried out in nine (FIG. 6) replicates. Data are presented as mean±standard error of mean (SEM). Group differences are evaluated by one-way ANOVA.

Results

SDL 11349 applied for 24 hours reduced the β-amyloid oligomer concentration in the medium significantly, by approximately 38-40% over a concentration range of 0.11 to 0.67 μM. The ANOVA was significant at p=0.009.

This experiment was performed by QPS Austria, Parkring 12, A-8074 Grambach, Austria.

Neurite Assessment
Procedures

Rat cortical neurons were cultured as described by Callizot et al (J Neurosci Res 2013, 91:706-716). On day 11 of culture, Aβ oligomer solution, 20 μM, was applied. The Aβ oligomer preparation, having an average weight of 90 kDa, prepared as described by Callizot et al (op cit) contained only diffusible species, not fibrils or protofibrils. Briefly, Aβ1-42 peptide at a concentration of 40 μM was dissolved in the culture medium, gently agitated for 3 days at 37° C. in the dark, and used immediately after dilution. SDL 11349 and BDNF (50 ng/ml) were dissolved in culture medium (maximum of 0.1% DMSO final concentration) then pre-incubated with primary cortical neurons for 24 h before the Aβ1-42 oligomer solution application.

The oligomers were incubated with the neurons and various concentrations of SDL 11349, or BDNF, 50 ng/ml, the positive control, for 24 hours, in 6 replicates per condition. Then the supernatant was removed and the neurons were fixed with a cold ethanol and acetic acid solution. The cells were permeabilized with 0.1% saponin and then incubated for 2 h with mouse monoclonal antibody and microtubule-associated protein 2 (MAP-2). Subsequently, Alexa-Fluor 488 goat anti-mouse IgG was applied, and images were obtained and analyzed automatically.

Results

The neurite network was reduced by 40% by the Aβ oligomer preparation. SDL 11349, at 1 μM, blocked the toxic effect of the Aβ oligomers, comparably to the protective effect of the positive control, BDNF, as shown in FIG. 7. Significant beneficial effects were seen from 0.66 to 4.0 μM SDL 11349. Data are presented as mean±standard error of the mean. Asterisks indicate *p<0.05, one way ANOVA followed by PLSD Fisher's test.

The effect of SDL 1 μM, can be appreciated in FIG. 8. The normal neurite network, as shown in FIG. 8 (a), becomes sparse when treated with Aβ oligomers as seen in 8 (b), BDNF, the "gold standard" for this assay, preserves the neurite network, panel (c), and SDL 11349 produces a result which is comparable to BDNF, panel 8 (d), and to the control well, panel 8 (a).

This work was performed at Neuro-Sys, 410 CD 60, Parc de l'Oratoire de Bouc, F-13120, Gardanne, France Dendritic Spine Assessment Dendritic spines are fundamental to cognitive processes and are decreased in areas of fibrillar amyloid deposits in the Alzheimer brain. (Gruntzendler et al, op cit)

Methods

Adult C57B16 mice, (8 weeks old) were administered vehicle or SDL 11349, 0.005, 0.03, 0.07, 0.1 or 0.2 mg/kg, ip, per day for five days prior to sacrifice after rapid anesthetization with isofluorane. Brain tissue was sectioned into 300 μM slices from anterior to posterior extremes.

Ballistic dye labelling was performed, followed by laser-scanning confocal microscopy (Olympus FV1000) using a 63× objective (1.42 NA) to scan individually labelled neurons at high resolution (0.103×0.103×0.33 μm voxels). Target neurons were identified in the brain region of interest by anatomical location and cell morphology. Microscopy was performed blind to experimental conditions. A minimum of 5 samples per animal were measured for each segment.

Afraxis ESP Dendritic Spine Analysis and Assessment of Dendritic Membrane Integrity.

Blind deconvolution (AutoQuant) was applied to raw three-dimensional digital images which were then analyzed for spine density and morphology by trained analysts. Individual spines were measured manually for (a) head diameter, (b) length, and (c) neck thickness from image Z-stacks using custom-built Afraxis ESP software. Each dendrite was analyzed by 3 independent analysts.

Automated image assignment software (C++) distributed images to analysts in a randomized manner and ensured that each analyst performed measurements of near equal numbers of dendrites per group. Analysts were blinded to all experimental conditions. Statistical analysis of interanalyst variability for each dendrite was examined online and used to eliminate dendrites that did not meet interanalyst reliability criteria: a dendrite was incorporated into the final analysis only if measurement distributions for all three measures failed to be significantly different between analysts. For spine density and spine morphological classification, data across analysts were averaged to report data for each dendrite. Data population values (N's) were reported from dendrites collected equally from all mice.

Statistics

Values are reported in tables and plots as group means±standard errors of the mean (SEMs). For all group comparisons of parametric values, statistical significance was determined using the analysis of variance test (ANOVA; SPSS). Post-hoc comparisons were assessed using the Student's t-test (2 tails). All Afraxis experimenters were fully blinded to treatment conditions during the collection, assembly and interpretation of the data. Non-parametric comparisons of individual measure population distributions were conducted using the 2-sample Kolmogorov-Smirnov test α=.0001).

Figure 9:
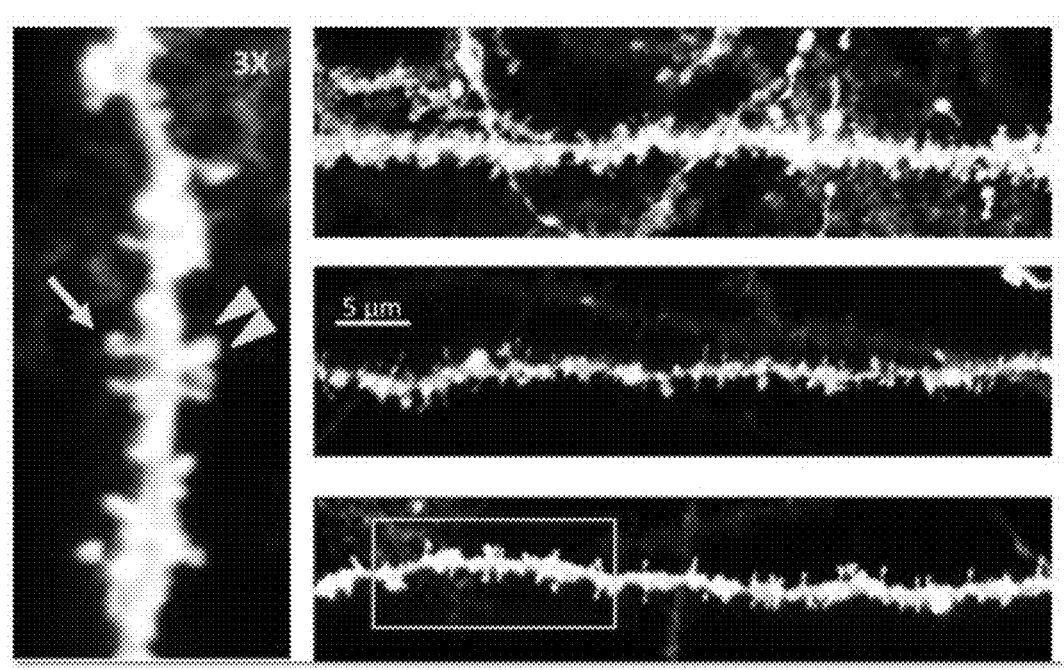
FIG. 9 is a representative laser-scanning confocal micrograph of apical dendrite from a pyramidal neuron in the CA1 region of the dorsal hippocampus showing multiple dendritic spines.

Dendritic spine morphology was analyzed from samples taken from secondary apical dendrites, and secondary basal dendrites of CA1 pyramidal neurons in the dorsal hippocampus. A representative laser-scanning confocal micrograph is shown in FIG. 9, showing a sampled position. From each animal, three sections were collected (derived between −1.4 and −2.9 mm from bregma) and five individually labelled neurons identified. A 50 μm segment was analyzed from each location.

Figure 10:
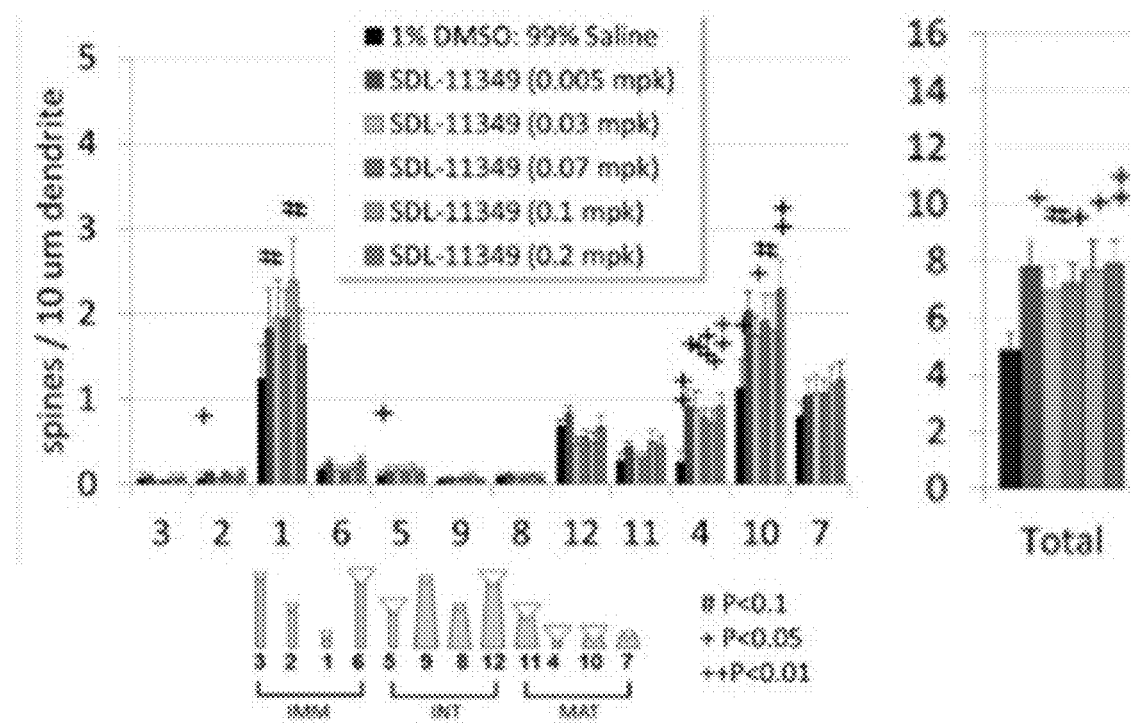
FIG. 10 shows that SDL 11349 treatment for 5 days significantly increases the number of spines on apical dendrites of pyramidal neurons in the CA1 region of the dorsal hippocampus of the mouse.

Total spine density values for each group are described in FIG. 10. All treatment groups expressed a statistically significant difference (p<0.05, 2-tailed t-test) or trend (p<.01) compared to vehicle controls in apical dendritic samples. There was no effect in basal samples. The magnitude of effect and reliability across all dose levels for SDL 11349 treatment is striking. Based on the magnitude of effect versus control, there does not appear to be a dose-dependent modification of spines by SDL 11349 within the range tested here.

Figure 11:
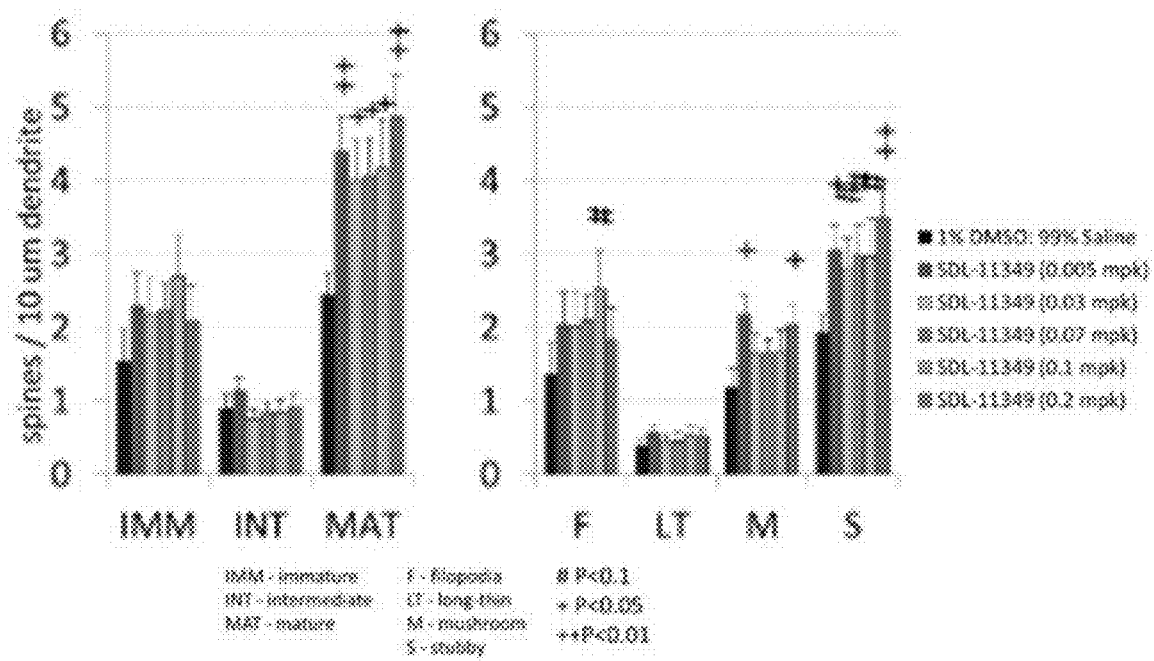
FIG. 11 shows that SDL 11349 treatment for 5 days specifically increases mature spines on apical dendrites of CA1 pyramical neurons in the dorsal hippocampus of the mouse

Dendritic spine maturity categories are described in FIG. 10 and shown in FIGS. 10 and 11. Raw dendritic spine morphometric values (spine length, head diameter, neck width) are assembled into a 12-category classification scheme that describes highly granulated dendritic spine phenotypes. These categories are collapsed to represent immature, intermediate and mature scores. Finally, an assessment independent from the 12-point scheme is used to describe classic spine phenotypes (e.g. mushroom stubby, etc.). The total spine density effect in apical dendritic samples was largely driven by changes to mature spine phenotypes. Ai treatment groups expressed significantly increased mature spine densities versus vehicle controls. This translated into generalized increases in stubby and mushroom spines.

This work was performed by Afraxis, 6605 Nancy Ridge Drive, Suite 224, San Diego, Calif. 92121.

The invention claimed is:

1. A method of reducing the decrease in Aβ42 in CSF of patients exhibiting a decreased Aβ42 level in CS but not exhibiting signs of dementia which comprises administering thereto a therapeutically acceptable dose of an analog of (4aS,6R,8aS)-5,6,9,10,11,12-hexahydro-3-methoxy-11-methyl-4aH-[1]benzofuro[2]benzazepin-6-ol of the formula:

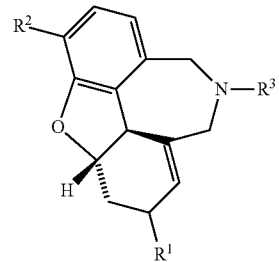

wherein $R^1$ is a mono alkyl carbamate group having from 1-10 carbon atoms in the alkyl group; $R^2$ is an alkoxy group of 1-6 carbon atoms, a hydroxy group; hydrogen, or an alkanoyloxy group of 2-10 carbon atoms, and $R^3$ is hydrogen or alkyl of 1 to 10 carbon atoms, or a pharmaceutically acceptable salt thereof.

2. A method as claimed in claim 1, wherein $R^2$ is methoxy and $R^3$ is methyl.

3. A method as claimed in claim 2, wherein said carbamate group is a mono alkyl carbamate of 2 to 8 carbon atoms.

4. A method as claimed in claim 2, wherein said carbamate group is n-butyl carbamate.

5. A method as claimed in claim 1, wherein said therapeutic dose of an active compound as described above is administered to patients having a CSF Aβ42 level of less than 192 pg/ml as measured by the Luminex INNO-BIA ARzBio3 assay.

6. A method as claimed in claim 1, wherein said therapeutic dose is selected to produce a concentration in brain of from 0.2 to 1.5 μm of said analog of (4aS,6R,8aS)-5,6,9,10,11,12-hexahydro-3-methoxy-11-methyl-4aH-[1]benzofuro[3a,3,2-ef] [2] benzazepin-6-ol.

7. A method as claimed in claim 1, wherein the daily dose of (4aS,6R,8aS)-5,6,9,10,11,12-hexahydro-3-methoxy-11-methyl-4aH-[1]benzofuro[3a,3,2-ef][2] benzazepin-6-ol analog is from 1-50 mg.

8. A method as claimed in claim 1, wherein the daily dose is administered as a divided dose from 2-4 times per day or as a controlled release dose.

9. A method of reducing the fail in Aβ42 in CSF of patients which comprises administering thereto a therapeutically acceptable dose of a compound of an analog of (4aS,6R,8aS)-5,6,9,10,11,12-hexahydro-3-methoxy-11-methyl-4aH-[1]benzofuro[3a,3,2-el][2] benzazepin-6-ol of the formula:

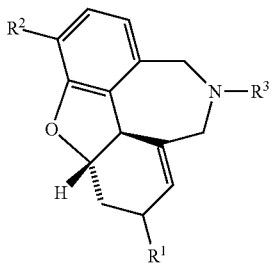

wherein $R^1$ is a monoalkyl carbamate group having from 1-10 carbon atoms in the alkyl group; $R^2$ is an alkoxy group of from one to six carbon atoms, a hydroxy group, hydrogen, or an alkanoyloxy group or 2 to 10 carbon atoms, and $R^3$ is hydrogen or alkyl of 1 to 10 carbon atoms or a pharmaceutically acceptable salt thereof to a patient who has been assessed by one or more standard tests: MMSE, ADAS-cog, Logical Memory Delayed Paragraph Recall, WAIS-R Digit Symbol Substitution, CDR-global, CIR-SB, NTB, logical memory IIA (delayed) and IA (immediate), category fluency, delayed and immediate word-list recall, progressive matrices, ELSMEM, CogState, trailmaking, executive function, neuromotor speed, ADCS-ADL, DAD, and others, or a composite test composed of elements of these or other tests, to have impaired cognition or function, but not to be displaying dementia, and not having a condition not associated with Alzheimer pathology to which the impaired cognition or function can be solely attributed so as to delay deterioration of cognition and/or function.

10. A method as claimed in claim 9, wherein $R^2$ is methoxy and $R^3$ is methyl.

11. A method as claimed in claim 10, wherein $R^1$ is n-butyl carbamate.

12. A method as claimed in claim 9, wherein said therapeutic dose is selected to produce a concentration in brain of from 0.2 to 1.5 μm of said analog of (4aS,6R,8aS )-5,6,9,10,11,12-hexahydro-3-methoxy-11-methyl-4aH-[1] benzofuro[3a,3,2-ef] [2] benzazepin-6-ol.

13. A method of reducing the fall in Aβ42 in CSF of patients but not exhibiting signs of dementia comprising administering thereto a therapeutically acceptable dose of a compound of an analog of (4aS,6R,8aS)-5,6,9,10,11,12-hexahydro-3-methoxy-11-methyl-4aH-[1]benzofuro[3a,3,2-ef] [2] benzazepin-6-ol of the formula:

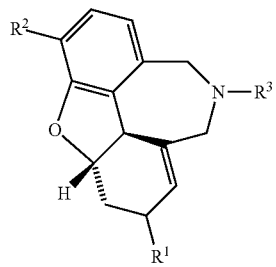

wherein $R^1$ is a monoalkyl carbamate having, from 1-10 carbon atoms in the alkylgroup; $6^2$ is an alkoxy group of from one to six carbon atoms, a hydroxy group, hydrogen; or an alkanoyloxy group of 2 to 10 carbon atoms; and $R^3$ is hydrogen or alkyl of 1 to 10 carbon atoms; or a pharmaceutically acceptable salt thereof to a patient having medial temporal lobe, paralimbic, and/or temporoparietal lobe atrophy on structural MRI, or decreased fluorodeoxyglucose uptake in the temporoparietal cortices on PET scan.

14. A method as claimed in claim 13, wherein $R^2$ is methoxy and $R^3$ is methyl.

15. A method as claimed in claim 14, wherein $R^1$ is n-butyl carbamate.

16. A method as claimed in claim 13, wherein said therapeutic dose is selectee; to produce a concentration in brain of from 0.2 to 1.5 μM of said analog of (4aS,6R,8aS)-5,6,9,10,11,12-hexahydro-3-methoxy-11-methyl-4aH-[1] benzofuro [3a,3,2-ef] [2] benzazepin-6-ol but not exhibiting signs of dementia.

17. A method of reducing the fall in Aβ42 in CSF of patients not exhibiting signs of dementia comprising administering a therapeutically acceptable dose of a compound of an analog of (4aS,6R,8aS)-5,6,9,10,11,12-hexahydro-3-methoxy-11-methyl-4aH-[1]benzofuro[3a,3,2-ef] [2] benzazepin-6-ol of the formula:

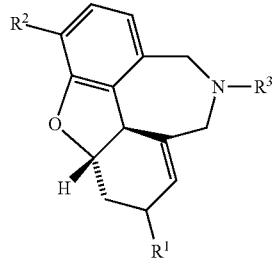

wherein $R^1$ is a monoalkyl having from 1-10 carbon atoms in the alky group; $R^2$ is an alkoxy group of from one to six carbon atoms, a hydroxy group, hydrogen, or an alkanoyloxy group of 2 to 10 carbon atoms; and $R^3$ is hydrogen or alkyl of 1 to 10 carbon atoms, or a pharmaceutically acceptable salt thereof to a patient whose CSF Aβ42 is decreasing.

18. A method as claimed in claim 17, wherein said $R^2$ is methoxy and $R^3$ is methyl.

19. A method as claimed in claim 18, wherein $R^1$ is n-butyl carbamate.

20. A method as claimed in claim 17, wherein said therapeutic dose is selected to produce a concentration in brain of from 0.2 to 1.5 μM of said analog of (4aS,6R,8aS)-5,6,9,10,11,12-hexahydro-3-methoxy-11-methyl-4aH-[1] benzofuro[3a,3,2-ef] [2] benzexpin-6-oL.

21. A method of treating patient not exhibiting signs of dementia which comprises administering a therapeutically acceptable dose of a compound of an analog of (4aS,6R,8aS )-5,6,9,10,11,12-hexahydro-3-methoxy-11-methyl-4aH-[1] benzofuro[3a,3,2-ef] [2] benzazepin-6-ol of the formula:

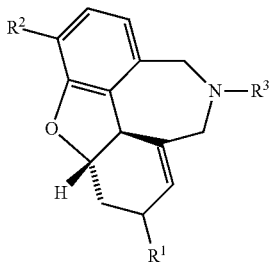

wherein R¹ is a monoalkyl carbamate having from 1-10 carbon atoms in the alkyl group; R² is an alkoxy group of from one to six carbon atoms, a hydroxy group, hydrogen, or an alkanoyloxy group of 2 to 10 carbon atoms and R³ is hydrogen or alkyl of 1 to 10 carbon atoms; or a pharmaceutically acceptable salt thereof to a patient in need thereof in combination with a nicotinic agonist in order to inhibit plaque deposition or aid in removal of plaques of Aβ, prevent the decrease or cause an increase in Aβ42 in CSF, delay progression to Alzheimer's disease dementia, or reduce the loss of cognition and/or activities of daily living.

22. A method as claimed in claim 21, wherein R² is methoxy and R³ is methyl.

23. A method as claimed in claim 22, wherein R¹ is n-butyl carbamate.

24. A method as claimed in claim 21, wherein said therapeutic dose is selected to produce a concentration in brain of from 0.2 to 1.5 µM of said analog of (4aS,6R,8aS)-5,6,9,10,11,12-hexahydro-3-methoxy-11-methyl-4aH-[1] benzofuro[3a,3,2-ef] [2] benzazepin-6-ol.

25. A method of treating an individual who has been determined to have the ApoE4 isoform of Apolipoprotein E which comprises administering thereto a therapeutically acceptable dose of a compound of an analog of (4aS,6R,8aS)-5,6,9,10,11,12-hexahydro-3-methoxy-11-methyl-4aH-[1]benzofuro[3a,3,2-ef][2]benzazepin-6-ol of the formula:

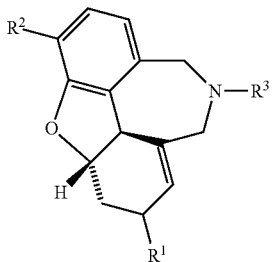

wherein R¹ is a monoalkyl carbamate having from 1-10 carbon atoms in the alkyl group; R2 is an alkoxy group of from one to six carbon atoms, a hydroxy group, hydrogen, or an alkanoyloxy group of 2 to 10 carbon atoms, and R³ is hydrogen or alkyl of 1 to 10 carbon atoms; or a pharmaceutically acceptable salt thereof to a patient who has been determined to have the ApoE4 isoform of Apolipoprotein E but who is not exhibiting signs of dementia in an amount sufficient to inhibit plaque deposition or aid in removal of plaques of Aβ, or to reduce the fall in CSF Aβ42, or prevent progression of cognitive and/or functional decline, or prevent progression to Alzheimer's dementia.

26. A method as claimed in claim 25, wherein R² is methoxy and R³ is methyl.

27. A method as claimed in claim 26, wherein R¹ is n-butyl carbamate.

28. A method as claimed in claim 25, wherein said therapeutic dose is selected to produce a concentration in brain of from 0.2 to 1.5 µM of said analog of (4aS,6R,8aS)-5,6,9,10,11,12-hexahydro-3-methoxy-11-methyl-4aH-[1] benzofuro[3a,3,2-ef] [2]benzazepin-6-ol.

29. A method of reducing the fall in Aβ42 in CSF of patients exhibiting a decreased Aβ42 level in CSF or one which is falling at >1%/year, or more than 10% from baseline, or falling on two successive postbaseline samples at least three months apart, but not exhibiting signs of dementia which comprises administering thereto a therapeutically acceptable dose of a compound of an analog of (4aS,6R,8aS)-5,6,9,10,11,12-hexahydro-3-methoxy-11-methyl-4aH-[1]benzofuro[3a,3,2-ef] [2] benzazepin-6-ol of the formula:

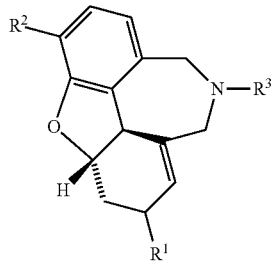

wherein R¹ is a monoalkyl carbamate having from 1-10 carbon atoms in the alkyl group; R² is an alkoxy group of from one to six carbon atoms, a hydroxy group, hydrogen, or an alkanoyloxy group of 2 to 10 carbon atoms and R³ is hydrogen or alkyl of 1 to 10 carbon atoms or a pharmaceutically acceptable salt thereof to a patient who has been determined to carry a fully-penetrant mutation which causes Alzheimer's dementia.

30. A method as claimed in claim 29, R² is methoxy and R³ is methyl.

31. A method as claimed in claim 30, wherein R¹ is n-butyl carbamate.

32. A method as claimed in claim 29, wherein said therapeutic dose is selected to produce a concentration in brain of from 0.2 to 1.5 µM of said analog of (4aS,6R,8aS)-5,6,9,10,11,12-hexahydro-3-methoxy-11-methyl-4aH-[1] benzofuro[3a,3,2-ef] [2]benzazepin-6-ol.

33. A method of reducing the fall in Aβ42 in CSF of patients exhibiting a decreased Aβ42 level in CSF, or a level failing by >1%/year, or 10% from baseline, or falling on two successive post-baseline samples at least 3 months apart, but not exhibiting signs of dementia which comprises administering thereto a therapeutically acceptable dose of a compound of an analog of (4aS,6R,8aS)-5,6,9,10,11,12-hexahydro-3-methoxy-11-methyl-4aH-[1] benzofuro[3a,3,2-ef] [2] benzazepin-6-ol of the formula:

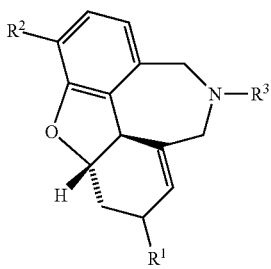

wherein R¹ is a monoalkyl carbamate having from 1-10 carbon atoms in the alkyl group; R² is an alkoxy group of from one to six carbon atoms, a hydroxy group, hydrogen, or an alkanoyloxy group of 2 to 10 carbon atoms and R¹ is hydrogen or alkyl of 1 to 10 carbon atoms or a pharmaceutically acceptable salt thereof;

to a patient who has not developed Alzheimer's dementia but who has been determined to have a potential for Alzheimer's disease based on lowered or falling CSF Aβ42 of >1%/year, or a 10% fall from baseline, or decreases from baseline on two successive postbaseline samples at least 3 months apart, reduced cognitive or functional ability beyond that expected for age, MRI or fluorodeoxyglucose PET Alzheimer-type changes, decrease of Aβ42 in CSF, increased or increasing Aβ amyloid in brain or presence of the APOE4 isoform of AApolipoprotein E or who have a penetrant mutation known to correlate with Alzheimer's dementia in co-administration with an agent which promotes clearance of Aβ antibodies or stimulating antibody production, or binding or resulting in binding to Aβ species, in order to enhance clearance of Aβ, enhance or slow the decline of cognitive and/or functional abilities, or retard conversion to Alzheimer's dementia.

34. A method as claimed in claim 33, wherein R² is methoxy and R³ is methyl.

35. A method as claimed in claim 34, wherein R¹ is n-butyl carbamate.

36. A method as claimed in claim 33, wherein said therapeutic dose is selected to produce a concentration in brain of from 0.2 to 1.5 μM of said analog of (4aS,6R,8aS)-5,6,9,10,11,12-hexahydro-3-methoxy-11-methyl-4aH-[1] benzofuro[3a,3,2-ef] [2] benzazepin-6-ol.

37. A method to improve performance or slow decline greater than expected for age in a patient not exhibiting signs of dementia which comprises administering thereto a therapeutically acceptable dose of a compound of an analog of (4aS,6R,8aS]-5,6,9,10,11,12-hexahydro-3-methoxy-11-methyl-4aH-[1] benzofuro[3a,3,2-ef] [2] benzazepin-6-ol of the formula:

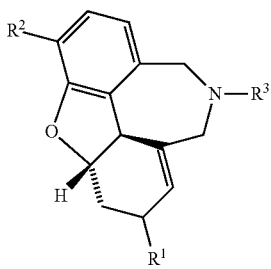

wherein R¹ is a monoalkyl carbamate having from 1-10 carbon atoms in the alkyl group; R² is an alkoxy group of from one to six carbon atoms, a hydroxy group, hydrogen, or an alkanoyloxy group of 2 to 10 carbon atoms and R³ is hydrogen or alkyl of 1 to 10 carbon atoms or a pharmaceutically acceptable salt thereof.

38. A method as claimed in claim 37, wherein R² is methoxy and R³ is methyl.

39. A method as claimed in claim 38, wherein R¹ is n-butyl carbamate.

40. A method as claimed in claim 37, ; wherein said therapeutic dose is selected to produce a concentration in brain of from 0.2 to 1.5 μM of said analog of (4aS,6R,8aS)-5,6,9,10,11,12-hexahydro-3-methoxy-11-methyl-4aH-[1] benzofuro[3a,3,2-ef] [2] benzazepin-6-ol.

41. A method to delay the onset of dementia in patients having a CSF Aβ to tau ratio below the discrimination line determined by Aβ42=240+1.18 ×tau, or a ratio of CSF Aβ$_{1-42}$ to tau less than 6.16, but not exhibiting signs of dementia which comprises administering thereto a therapeutically acceptable dose of a compound of an analog of (4aS,6R,8aS)-5,6,9,10,11,12-hexahydro-3-methoxy-11-methyl-4aH-[1] benzofuro[3a,3,2-ef] [2] benzazepin-6-6-ol of the formula:

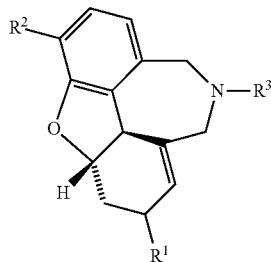

wherein R¹ is a monoalkyl carbamate having from 1-10 carbon atoms in the alkyl group; R² is an alkoxy group of from one to six carbon atoms, a hydroxy group, hydrogen, or an alkanoyloxy group of 2 to 10 carbon atoms, and R³ is hydrogen or alkyl of 1 to 10 carbon atoms or a pharmaceutically acceptable salt thereof.

42. A method as claimed in claim 41, wherein R² is methoxy and R³ is methyl.

43. A method as claimed in claim 42, wherein R¹ is n-butyl carbamate.

44. A method as claimed in claim 41, wherein said therapeutic dose is selected to produce a concentration in brain of from 0.2 to 1.5 μM of said analog of (4aS,6R,8aS)-5,6,9,10,11,12-hexahydro-3-methoxy-11-methyl-4aH-[1] benzofuro[3a,3,2-ef][2] benzaepin-6-ol.

45. A method as claimed in claim 17 wherein said decrease in CSF Aβ42 is determined by a drop of >1%/year when the lumbar puncture is done at the same time of day, or 10% from baseline, or decreases on two successive post-baseline samplings, in order to reduce the rate of decrease.

46. A method as claimed in claim 37 wherein improved performance, or slowing in decline greater than expected for age, is determined by a test selected from the group consisting of the MMSE, ADAS-cog, Logical Memory Delayed Paragraph Recall, WAIS-R Digit Symbol Substitution, CDR-global, CDR-SB, NTB, logical memory IIA (delayed) and IA (immediate), category fluency, delayed and immediate word-list recall, progressive matrices, ELSM EM, CogState, trailmaking, executive function, neuromotor speed, ADCS-ADL, DAD, and a combination of elements of these or other cognitive and/or functional tests.

47. The method as claimed in claim 33, wherein the agent which promotes clearance of Aβ antibodies or stimulating antibody production, or binding or resulting in binding to Aβ species, comprises at least one of solanezurnab, aducanumab, or ganterenumab.

* * * * *